(12) United States Patent
Taguchi et al.

(10) Patent No.: US 12,275,705 B2
(45) Date of Patent: Apr. 15, 2025

(54) PYRIDINIUM SALTS AND PEST CONTROL AGENT

(71) Applicant: Nippon Soda Co., Ltd., Tokyo (JP)

(72) Inventors: Riho Taguchi, Odawara (JP); Hiroto Suzuki, Odawara (JP); Kotaro Shibayama, Odawara (JP); Takao Iwasa, Odawara (JP); Kento Iwata, Odawara (JP)

(73) Assignee: NIPPON SODA CO., LTD., Tokyo (JP)

( * ) Notice: Subject to any disclaimer, the term of this patent is extended or adjusted under 35 U.S.C. 154(b) by 715 days.

(21) Appl. No.: 17/612,161

(22) PCT Filed: May 26, 2020

(86) PCT No.: PCT/JP2020/020665
§ 371 (c)(1),
(2) Date: Nov. 17, 2021

(87) PCT Pub. No.: WO2020/241614
PCT Pub. Date: Dec. 3, 2020

(65) Prior Publication Data
US 2022/0213039 A1    Jul. 7, 2022

(30) Foreign Application Priority Data

May 29, 2019  (JP) ................................. 2019-100653
May 29, 2019  (JP) ................................. 2019-100656

(51) Int. Cl.
*C07D 213/89*    (2006.01)
*A01N 43/40*     (2006.01)
(Continued)

(52) U.S. Cl.
CPC .......... *C07D 213/89* (2013.01); *A01N 43/40* (2013.01); *A01N 43/42* (2013.01); *A01N 43/78* (2013.01);
(Continued)

(58) Field of Classification Search
CPC ................................................... C07D 213/89
(Continued)

(56) References Cited

U.S. PATENT DOCUMENTS 4,013,669 A * 3/1977 Parsons ................ C07D 213/89
546/281.4
4,025,632 A * 5/1977 Parsons ................ C07D 213/89
514/358

(Continued)

FOREIGN PATENT DOCUMENTS

CN    1130900 A     9/1996
CN    102686573 A    9/2012
(Continued)

OTHER PUBLICATIONS

Tamura et al., Yakugaku Zasshi (1971), 91(1), 72-80.*
Lown et al., Canadian Journal of Chemistry (1972), 50(4), 584-90.*
Redda et al., Journal of Pharmaceutical Sciences (1992), 81(5), 463-6.*
Davies et al., Angewandte Chemie, International Edition (2011), 50(38), 8931-8935.*
Office Action dated Jun. 7, 2023, in TW 2020117403, with English translation.
(Continued)

*Primary Examiner* — Niloofar Rahmani
(74) *Attorney, Agent, or Firm* — FITCH, EVEN, TABIN & FLANNERY LLP

(57) ABSTRACT

A compound represented by a formula (I) or a formula (II):

(Chemical Formula 1)

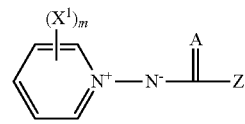

(I)

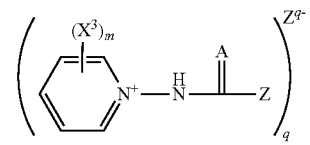

(II)

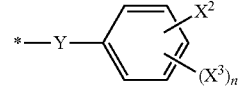

(Z-1)

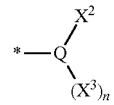

(Z-2)

(in the formulas (I) and (II), A represents an oxygen atom or a sulfur atom, $X^1$ represents a halogeno group or the like, m represents the number of $X^1$ groups and is any integer of 0 to 5, Z represents a group represented by a formula (Z-1) or a formula (Z-2), a bond marked with a symbol * means a bond with a carbonyl group or a thiocarbonyl group in a pyridinium salt, Y represents a substituted or unsubstituted $C_{2-6}$ alkenylene group, Q represents a naphthalene ring or a 6- to 10-membered heteroaryl ring, $X^2$ represents a substituted or unsubstituted $C_{1-6}$ alkyl group or the like, $X^3$ represents a halogeno group or the like, n represents the number of $X^3$ groups and is any integer of 0 to 4, $Z^{q-}$ represents a counter ion, and q represents a valence of the counter ion and is 1 or 2.)

5 Claims, No Drawings

(51) Int. Cl.
| | |
|---|---|
| A01N 43/42 | (2006.01) |
| A01N 43/78 | (2006.01) |
| A01P 7/02 | (2006.01) |
| A01P 7/04 | (2006.01) |
| C07D 405/12 | (2006.01) |
| C07D 409/12 | (2006.01) |
| C07D 417/12 | (2006.01) |

(52) U.S. Cl.
CPC ...... *A01P 7/02* (2021.08); *A01P 7/04* (2021.08); *C07D 405/12* (2013.01); *C07D 409/12* (2013.01); *C07D 417/12* (2013.01)

(58) Field of Classification Search
USPC .......................................................... 546/255
See application file for complete search history.

(56) References Cited

U.S. PATENT DOCUMENTS

| | | | |
|---|---|---|---|
| 4,088,653 A * | 5/1978 | Knaus | C07D 213/89 546/249 |
| 4,125,617 A | 11/1978 | Parsons | |
| 4,138,548 A | 2/1979 | Parsons | |
| 5,877,322 A | 3/1999 | Reuschling et al. | |
| 2011/0009263 A1 | 1/2011 | Waldraff et al. | |
| 2011/0301355 A1 | 12/2011 | Miyashita et al. | |
| 2012/0289403 A1 | 11/2012 | Soergel et al. | |
| 2015/0005347 A1 | 1/2015 | Kagabu et al. | |
| 2020/0275655 A1 | 9/2020 | Iwasa et al. | |

FOREIGN PATENT DOCUMENTS

| | | |
|---|---|---|
| CN | 104220424 A | 12/2014 |
| CN | 111465596 B | 9/2023 |
| GB | 1 419 377 A | 12/1975 |
| JP | 48-077026 A | 10/1973 |
| JP | 04-338387 A | 11/1992 |
| TW | 201002207 A1 | 1/2010 |
| WO | WO-2007/015533 A1 | 2/2007 |
| WO | WO-2019/107348 A1 | 6/2019 |
| WO | WO-2020/241614 A1 | 12/2020 |
| WO | WO-2020/241632 A1 | 12/2020 |

OTHER PUBLICATIONS

Office Action and Search Report dated Oct. 28, 2022 in CN 201880075410.9.
Office Action dated Aug. 2, 2022 in JP 2019-557234, with English translation.
Database Registry [Online], CAS Registry No. 157891-27-5, Sep. 23, 1994.
Database Registry [Online], CAS Registry No. 157891-29-7, Sep. 23, 1994.
Guzel et al., "Discovery of Low Nanomolar and Subnanomolar Inhibitors of the Mycobacterial beta-Carbonic Anhydrases Rv1284 and Rv3273," Journal of Medicinal Chemistry, 2009, 52:4063-4067.
Office Action dated Nov. 8, 2023 in KR 10-2020-7014475, with English translation.
Abramovitch et al., "Photolytic Generation of N-Acylnitrenium Ions Under Neutral Conditions: Synthesis of Polycyclic Lactams," Heterocycles, 1994, 37(3):1463-1466.
Gangapuram et al., "Synthesis and Biological Evaluation of Substituted N-[3-(1H-Pyrrol-1-yl)methyl]-1,2,5,6-tetrahydropyridin-1-yl]benzamide/benzene Sulfonamides as Anti-Inflammatory Agents," Arch. Pharm. Chem. Life Sci., 2014, 347:360-369.
Guest et al., "Synthesis and Biological Activity of 3-(N-Substituted Pyridinium-4-Thiomethyl)-7alpha-Formamido Cephalosporins," The Journal of Antibiotics, 1993, 64(8):1279-1288.
Guzel et al., "Carbonic anhydrase inhibitors. Synthesis of 2,4,6-trimethylpyridinium derivatives of 2-(hydrazinocarbonyl)-3-aryl-1H-indole-5-sulfonamides acting as potent inhibitors of the tumor-associated isoform IX and XII," Bioorganic & Medicinal Chemistry Letters, 2009, 19:2931-2934.
International Search Report dated Aug. 11, 2020 in PCT/JP2020/020665, with English translation.
International Search Report dated Feb. 12, 2019 in PCT/JP2018/043554, with English translation.
International Search Report dated Jul. 28, 2020 in PCT/JP2020/020719, with English translation.
Jezierska et al., "Synthesis, X-ray Crystallography and Computer-Aided Design Study of 5-Amino-3-methylisoxazole-4-carboxylic Acid N-2,4,6-Trimethylpyridinium)amide Chlorate(VII) Salt and Its Analogues," Polish J. Chem., 2003, 77:1461-1471.
Kakehi et al., "Preparation of New Nitrogen-Bridged Heterocycles. 43. Synthesis and Reaction of 4aH-Pyrido[1,2-3][1,3,4]thiadiazepine Derivatives," J. Org. Chem., 1997, 62:7788-7793.
Kise et al., "Mesomorphic Properties of N-4-Ethylpyridinio)-4-Alkoxybenzamidates: Ylide as a Liquid Crystal," Chemistry Letters, 1978, 11:1235-1238.
Mochona et al., "Synthesis and Anti-Inflammatory Activities of N-Benzoylamino-1,2,3,6-Tetrahydropyridine analogs," Drugs Under Experimental and Clinical Research, 2003, 29(4):131-140.
Office Action dated Dec. 24, 2019, in TW 107142602, with English translation.
Office Action dated Sep. 1, 2021 in U.S. Appl. No. 16/764,253.
STN Registry file, May 7, 2004, RN 680623-06-7, 3 pages.
STN Registry file, Nov. 16, 1984, RN 62088-48-6, 3 pages.
STN Registry File, Nov. 16, 1984, RN 62088-50-0, 3 pages.
Yeung et al., "Synthesis of N-[[(Substituted-phenyl)carbonyl]amino]-1,2,3,6-tetrahydropyridines with Analgesic and Hyperglycemic Activity," J. Med. Chem., 1982, 25:720-723.
Yeung et al., "Synthesis of N-Carbonylamino)-1,2,3,6-tetrahydropyridines with Analgesic, Antiinflammatory, and Hyperglycemic Activity," J. Med. Chem., 1982, 25:191-195.
Office Action dated Oct. 11, 2024 in VN App. No. 1-2020-02571.
Database Registry [Online], CAS Registry No. 62088-49-7 (Nov. 16, 1984).
Database Registry [Online], CAS Registry No. 62088-51-1 (Nov. 16, 1984).
Office Action dated Feb. 10, 2025 in KR Application No. 10-2021-7037594.

* cited by examiner

PYRIDINIUM SALTS AND PEST CONTROL AGENT

TECHNICAL FIELD

The present invention relates to a pyridinium salt and a pest control agent. More specifically, the present invention relates to a pyridinium salt which has excellent insecticidal activity and/or acaricidal activity, is excellent in safety and can be synthesized in an industrially favorable manner, and a pest control agent containing this pyridinium salt as an active ingredient.

CROSS-REFERENCE TO RELATED APPLICATIONS

This application is the U.S. National Stage of PCT/JP2020/020665, filed May 26, 2020, which claims priority to Japanese Patent Application No. 2019-100656 and Japanese Patent Application No. 2019-100653, filed May 29, 2019, the contents of which are incorporated herein by reference.

BACKGROUND ART

Various compounds having insecticidal/acaricidal activity have been proposed. In order to put such a compound to practical use as an agricultural chemical, it is required not only to have sufficiently high efficacy, but also to be unlikely to cause drug resistance, not to cause phytotoxicity to plants or soil pollution, and to have low toxicity to livestock and fish, or the like.

Incidentally, Patent Document 1 discloses a compound represented by a formula
(A) having acaricidal activity, and the like.

(Chemical Formula 1)

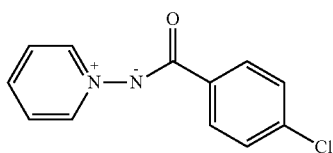

(A)

Further, Non-Patent Document 1 discloses a compound represented by a formula (B) having analgesic activity, and the like.

(Chemical Formula 2)

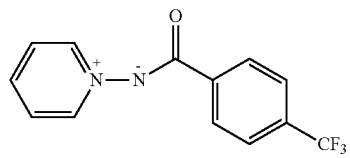

(B)

CITATION LIST

Patent Document

[Patent Document 1] U.S. Pat. No. 4,138,548

Non-Patent Document

[Non-Patent Document 1] Journal of Medicinal Chemistry, 1982, vol. 25, p 720-723

SUMMARY OF INVENTION

Technical Problem

An object of the present invention is to provide a pyridinium salt which is excellent in pest control activity, in particular, insecticidal activity and/or acaricidal activity, excellent in safety and can be synthesized in an industrially favorable manner. Another object of the present invention is to provide a pest control agent, an insecticidal or acaricidal agent, an ectoparasite control agent, or an endoparasite control- or exterminating agent containing a pyridinium salt as an active ingredient.

Solution to Problem

As a result of intensive studies in order to solve the above problems, the present invention including the following embodiments has been completed.

[1] A compound represented by a formula (I) or a formula (II):

[Chemical Formula 3]

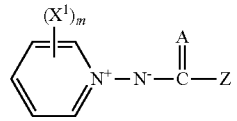

(I)

[Chemical Formula 4]

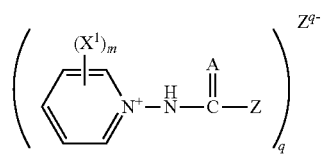

(II)

(in the formulas (I) and (II),

A represents an oxygen atom or a sulfur atom;

$X^1$ represents a halogeno group, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{1-6}$ alkoxy group, a substituted or unsubstituted $C_{2-6}$ alkenyloxy group, a substituted or unsubstituted $C_{2-6}$ alkynyloxy group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{3-8}$ cycloalkyl group, a substituted or unsubstituted $C_{6-10}$ aryl group, a substituted or unsubstituted $C_{6-10}$ aryloxy group, a substituted or unsubstituted 5- to 6-membered heteroaryl group, a substituted or unsubstituted 5- to 6-membered heteroaryloxy group, a group represented by $R^aR^bN—$, a group represented by $R^aR^bN—CO—$, a group represented by $R^cCO—NH—$, a pentafluorosulfanyl group, a nitro group or a cyano group;

$R^a$ represents a hydrogen atom, a substituted or unsubstituted $C_{1-6}$ alkyl group, or a substituted or unsubstituted $C_{6-10}$ aryl group, $R^b$ represents a hydrogen atom, a substituted or unsubstituted $C_{1-6}$ alkyl group, or a substituted or unsubstituted $C_{6-10}$ aryl group, $R^c$ represents a hydrogen atom, a substituted or unsubstituted $C_{1-6}$ alkyl group, or a substituted or unsubstituted $C_{6-10}$ aryl group, m represents the number of $X^1$ groups and is any integer of 0 to 5; and Z represents a group represented by a formula (Z-1) or a formula (Z-2), (Chemical Formula 5)

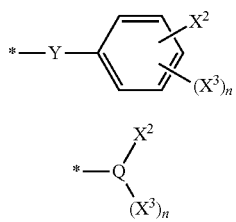

(Z-1)

(Z-2)

a bond marked with a symbol * means a bond with a carbonyl group or a thiocarbonyl group in a pyridinium salt, Y represents a substituted or unsubstituted $C_{2-6}$ alkenylene group, Q represents a naphthalene ring or a 6- to 10-membered heteroaryl ring, $X^2$ represents a substituted or unsubstituted $C_{1-6}$ alkyl group, a substituted or unsubstituted $C_{2-6}$ alkenyl group, a substituted or unsubstituted $C_{2-6}$ alkynyl group, a hydroxyl group, a substituted or unsubstituted $C_{1-6}$ alkoxy group, a substituted or unsubstituted $C_{2-6}$ alkenyloxy group, a substituted or unsubstituted $C_{2-6}$ alkynyloxy group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{3-8}$ cycloalkyl group, a substituted or unsubstituted $C_{6-10}$ aryloxy group, a substituted or unsubstituted 5- to 6-membered heteroaryloxy group, a group represented by $R^{a1}R^{b1}N—$, a group represented by $R^{a1}R^{b1}N—CO—$, a group represented by $R^{c1}CO—NH—$, a group represented by $R^{d1}O—N=CR^{f1}—$, a pentafluorosulfanyl group, a nitro group or a cyano group, $R^{a1}$ represents a hydrogen atom, a substituted or unsubstituted $C_{1-6}$ alkyl group, or a substituted or unsubstituted $C_{6-10}$ aryl group, $R^{b1}$ represents a hydrogen atom, a substituted or unsubstituted $C_{1-6}$ alkyl group, or a substituted or unsubstituted $C_{6-10}$ aryl group, $R^{c1}$ represents a hydrogen atom, a substituted or unsubstituted $C_{1-6}$ alkyl group, or a substituted or unsubstituted $C_{6-10}$ aryl group, $R^{d1}$ represents a hydrogen atom or a substituted or unsubstituted $C_{1-6}$ alkyl group, $R^{f1}$ represents a hydrogen atom or a substituted or unsubstituted $C_{1-6}$ alkyl group, $X^3$ represents a halogeno group, a substituted or unsubstituted $C_{1-6}$ alkyl group, a hydroxyl group, a substituted or unsubstituted $C_{1-6}$ alkoxy group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a pentafluorosulfanyl group, a nitro group, or a cyano group, n represents the number of $X^3$ groups and is any integer of 0 to 4, $Z^{q-}$ represents a counter ion, and q represents a valence of the counter ion and is 1 or 2.)

[2] The compound according to the above [1], wherein the compound represented by the formula (I) is a compound represented by a formula (I-1) and the compound represented by the formula (II) is a compound represented by a formula (II-1).

[Chemical Formula 6]

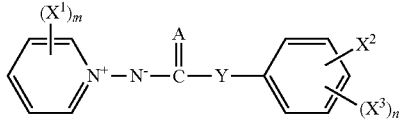

(I-1)

[Chemical Formula 7]

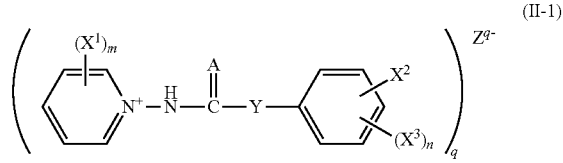

(II-1)

(In the formula (I-1) and formula (II-1),

A, $X^1$, m, Y, $X^2$, $X^3$, n, $Z^{q-}$, and q have the same meanings as those defined in the above [1].)

[3] The compound according to the above [1], wherein the compound represented by the formula (I) is a compound represented by a formula (I-2) and the compound represented by the formula (II) is a compound represented by a formula (II-2).

(Chemical Formula 8)

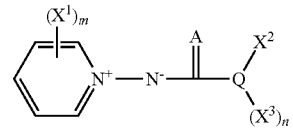

(I-2)

(Chemical Formula 9)

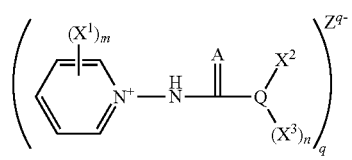

(II-2)

(In the formula (I-2) and formula (II-2),

A, $X^1$, m, Q, $X^2$, $X^3$, n, $Z^{q-}$, and q have the same meanings as those defined in the above [1].)

[4] A pest control agent containing at least one selected from the compounds according to any one of the above [1] to [3] as an active ingredient.

[5] An insecticidal or acaricidal agent containing at least one selected from the compounds according to any one of the above [1] to [3] as an active ingredient.

[6] An ectoparasite control agent containing at least one selected from the compounds according to any one of the above [1] to [3] as an active ingredient.

[7] An endoparasite control or exterminating agent containing at least one selected from the compounds according to any one of the above [1] to [3] as an active ingredient.

Advantageous Effects of Invention

The pyridinium salt of the present invention has a function of controlling pests which are problematic in terms of agricultural crops and hygiene. A control agent containing the pyridinium salt of the present invention can effectively control pests, especially agricultural pests and mites and ticks at a lower concentration, and can also effectively control ectoparasites and endoparasites that may harm humans and animals.

DESCRIPTION OF EMBODIMENTS

A pyridinium salt of the present invention is a compound represented by a formula (I) (inner salt) or a compound represented by a formula (II) (intermolecular salt). An inner salt is a compound having a cation center and an anion center in one molecule, that is, a zwitterion. An intermolecular salt is a compound formed by ion association of a cation and an anion, that is, an ion pair.

(Chemical Formula 10)

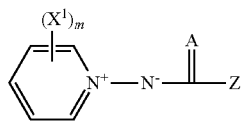

(I)

(Chemical Formula 11)

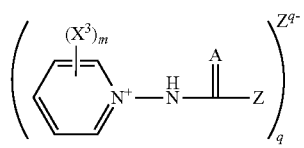

(II)

Here, the term "unsubstituted" means that it is composed only of a group which becomes a mother nucleus. When it is described only by the name of the group which becomes the mother nucleus without being described as "substituted", it means "unsubstituted" unless otherwise stated.

On the other hand, the term "substituted" means that any hydrogen atom of a group which becomes a mother nucleus is substituted with a group (substituent) having the same or different structure as that of the mother nucleus. Therefore, a "substituent" is another group bonded to a group which becomes a mother nucleus. The number of substituents may be one, or two or more. The two or more substituents may be the same or different.

The terms "$C_{1-6}$" and the like mean that the number of carbon atoms in the group which becomes a mother nucleus is 1 to 6, and so on. The number of carbon atoms does not include the number of carbon atoms present in the substituent. For example, a butyl group having an ethoxy group as a substituent is classified as a C2 alkoxy C4 alkyl group.

A "substituent" is not particularly limited as long as it is chemically acceptable and has the effects of the present invention. Hereinafter, groups which can be a "substituent" are exemplified.

A $C_{1-6}$ alkyl group such as a methyl group, an ethyl group, an n-propyl group, an i-propyl group, an n-butyl group, an s-butyl group, an i-butyl group, a t-butyl group, an n-pentyl group, and an n-hexyl group;

a $C_{2-6}$ alkenyl group such as a vinyl group, a 1-propenyl group, a 2-propenyl group (allyl group), a 1-butenyl group, a 2-butenyl group, a 3-butenyl group, a 1-methyl-2-propenyl group, and a 2-methyl-2-propenyl group;

a $C_{2-6}$ alkynyl group such as an ethynyl group, a 1-propynyl group, a 2-propynyl group, a 1-butynyl group, a 2-butynyl group, a 3-butynyl group, and a 1-methyl-2-propynyl group;

a $C_{3-8}$ cycloalkyl group such as a cyclopropyl group, a cyclobutyl group, a cyclopentyl group, a cyclohexyl group, and a cubanyl group;

a $C_{6-10}$ aryl group such as a phenyl group and a naphthyl group;

a $C_{6-10}$ aryl $C_{1-6}$ alkyl group such as a benzyl group and a phenethyl group;

a 3- to 6-membered heterocyclyl group;

a 3- to 6-membered heterocyclyl $C_{1-6}$ alkyl group;

a hydroxyl group;

a $C_{1-6}$ alkoxy group such as a methoxy group, an ethoxy group, an n-propoxy group, an i-propoxy group, an n-butoxy group, an s-butoxy group, an i-butoxy group, and a t-butoxy group;

a $C_{2-6}$ alkenyloxy group such as a vinyloxy group, an allyloxy group, a propenyloxy group, and a butenyloxy group;

a $C_{2-6}$ alkynyloxy group such as an ethynyloxy group and a propargyloxy group;

a $C_{6-10}$ aryloxy group such as a phenoxy group and a naphthoxy group;

a $C_{6-10}$ aryl $C_{1-6}$ alkoxy group such as a benzyloxy group and a phenethyloxy group;

a 5- to 6-membered heteroaryloxy group such as a thiazolyloxy group and a pyridyloxy group;

a 5- to 6-membered heteroaryl $C_{1-6}$ alkyloxy group such as a thiazolylmethyloxy group and a pyridylmethyloxy group;

a formyl group;

a $C_{1-6}$ alkylcarbonyl group such as an acetyl group and a propionyl group;

a formyloxy group;

a $C_{1-6}$ alkylcarbonyloxy group such as an acetyloxy group and a propionyloxy group;

a $C_{6-10}$ arylcarbonyl group such as a benzoyl group;

a $C_{1-6}$ alkoxycarbonyl group such as a methoxycarbonyl group, an ethoxycarbonyl group, an n-propoxycarbonyl group, an i-propoxycarbonyl group, an n-butoxycarbonyl group and a t-butoxycarbonyl group;

a $C_{1-6}$ alkoxycarbonyloxy group such as a methoxycarbonyloxy group, an ethoxycarbonyloxy group, an n-propoxycarbonyloxy group, an i-propoxycarbonyloxy group, an n-butoxycarbonyloxy group and a t-butoxycarbonyloxy group;

a carboxyl group;

a halogeno group such as a fluoro group, a chloro group, a bromo group, and an iodo group;

a $C_{1-6}$ haloalkyl group such as a chloromethyl group, a chloroethyl group, a trifluoromethyl group, a 1,2-dichloro-n-propyl group and a 1-fluoro-n-butyl group;

a $C_{2-6}$ haloalkenyl group such as a 2-chloro-1-propenyl group and a 2-fluoro-1-butenyl group;

a $C_{2-6}$ haloalkynyl group such as a 4,4-dichloro-1-butynyl group, a 4-fluoro-1-pentynyl group, and a 5-bromo-2-pentynyl group;

a $C_{1-6}$ haloalkoxy group such as a trifluoromethoxy group, a 2-chloro-n-propoxy group, and a 2,3-dichlorobutoxy group;

a $C_{2-6}$ haloalkenyloxy group such as a 2-chloropropenyloxy group and a 3-bromobutenyloxy group;

a $C_{1-6}$ haloalkylcarbonyl group such as a chloroacetyl group, a trifluoroacetyl group and a trichloroacetyl group;

an amino group;

a $C_{1-6}$ alkyl-substituted amino group such as a methylamino group, a dimethylamino group and a diethylamino group;

a $C_{6-10}$ arylamino group such as an anilino group and a naphthylamino group;

a $C_{6-10}$ aryl $C_{1-6}$ alkylamino group such as a benzylamino group and a phenethylamino group;

a formylamino group;

a $C_{1-6}$ alkylcarbonylamino group such as an acetylamino group, a propanoylamino group, a butyrylamino group and an i-propylcarbonylamino group;

a $C_{1-6}$ alkoxycarbonylamino group such as a methoxycarbonylamino group, an ethoxycarbonylamino group, an n-propoxycarbonylamino group and an i-propoxycarbonylamino group;

an unsubstituted or substituted aminocarbonyl group such as an aminocarbonyl group, a dimethylaminocarbonyl group, a phenylaminocarbonyl group and an N-phenyl-N-methylaminocarbonyl group;

an imino $C_{1-6}$ alkyl group such as an iminomethyl group, a (1-imino)ethyl group and a (1-imino)-n-propyl group;

a substituted or unsubstituted N-hydroxyimino $C_{1-6}$ alkyl group such as an N-hydroxy-iminomethyl group, a (1-(N-hydroxy)-imino)ethyl group, a (1-(N-hydroxy)-imino)propyl group, an N-methoxy-iminomethyl group, and a (1-(N-methoxy)-imino)ethyl group;

an aminocarbonyloxy group;

a $C_{1-6}$ alkyl-substituted aminocarbonyloxy group such as an ethylaminocarbonyloxy group and a dimethylaminocarbonyloxy group;

a mercapto group;

a $C_{1-6}$ alkylthio group such as a methylthio group, an ethylthio group, an n-propylthio group, an i-propylthio group, an n-butylthio group, an i-butylthio group, an s-butylthio group and a t-butylthio group;

a $C_{1-6}$ haloalkylthio group such as a trifluoromethylthio group and a 2,2,2-trifluoroethylthio group;

a $C_{6-10}$ arylthio group such as a phenylthio group and a naphthylthio group;

a 5- to 6-membered heteroarylthio group such as a thiazolylthio group and a pyridylthio group;

a $C_{1-6}$ alkylsulfinyl group such as a methylsulfinyl group, an ethylsulfinyl group and a t-butylsulfinyl group;

a $C_{1-6}$ haloalkylsulfinyl group such as a trifluoromethylsulfinyl group and a 2,2,2-trifluoroethylsulfinyl group;

a $C_{6-10}$ arylsulfinyl group such as a phenylsulfinyl group;

a 5- to 6-membered heteroarylsulfinyl group such as a thiazolylsulfinyl group and a pyridylsulfinyl group;

a $C_{1-6}$ alkylsulfonyl group such as a methylsulfonyl group, an ethylsulfonyl group and a t-butylsulfonyl group;

a $C_{1-6}$ haloalkylsulfonyl group such as a trifluoromethylsulfonyl group and a 2,2,2-trifluoroethylsulfonyl group;

a $C_{6-10}$ arylsulfonyl group such as a phenylsulfonyl group;

a 5- to 6-membered heteroarylsulfonyl group such as a thiazolylsulfonyl group and a pyridylsulfonyl group;

a $C_{1-6}$ alkylsulfonyloxy group such as a methylsulfonyloxy group, an ethylsulfonyloxy group and a t-butylsulfonyloxy group;

a $C_{1-6}$ haloalkylsulfonyloxy group such as a trifluoromethylsulfonyloxy group and a 2,2,2-trifluoroethylsulfonyloxy group;

a tri $C_{1-6}$ alkyl-substituted silyl group such as a trimethylsilyl group, a triethylsilyl group and a t-butyldimethylsilyl group;

a tri $C_{6-10}$ aryl-substituted silyl group such as a triphenylsilyl group;

a pentafluorosulfanyl group;

a cyano group; a nitro group.

Further, in these "substituents", any hydrogen atom in the substituent may be substituted with a group having a different structure. Examples of the "substituent" in this case include a $C_{1-6}$ alkyl group, a $C_{1-6}$ haloalkyl group, a $C_{1-6}$ alkoxy group, a $C_{1-6}$ haloalkoxy group, a halogeno group, a cyano group and a nitro group.

Further, the above-described "3- to 6-membered heterocyclyl group" includes 1 to 4 hetero atoms selected from the group consisting of a nitrogen atom, an oxygen atom and a sulfur atom as constituent atoms of the ring. The heterocyclyl group may be either monocyclic or polycyclic. As long as the polycyclic heterocyclyl group includes at least one heterocyclic ring, the remaining ring may be any of a saturated alicyclic ring, an unsaturated alicyclic ring or an aromatic ring. Examples of the "3- to 6-membered heterocyclyl group" include a 3- to 6-membered saturated heterocyclyl group, a 5- to 6-membered heteroaryl group, and a 5- to 6-membered partially unsaturated heterocyclyl group.

Examples of the 3- to 6-membered saturated heterocyclyl group include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, and a dioxanyl group.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group and a tetrazolyl group.

Examples of the 6-membered heteroaryl group include a pyridyl group, a pyrazinyl group, a pyrimidinyl group, a pyridazinyl group and a triazinyl group.

In the formula (II), $Z^{q-}$ represents a counter ion, and q represents a valence of the counter ion and is 1 or 2. Specific examples of a monovalent anion $Z^-$ include $Cl^-$, $Br^-$, $I^-$, $NO_3^-$, $CH_3COO^-$, $CH_3SO_3^-$, $CF_3SO_3^-$ and $TolSO_3^-$. Specific examples of a divalent anion $Z^{2-}$ include $SO_4^{2-}$ and the like. Tol is an abbreviation indicating an o-methylphenyl group, an m-methylphenyl group or a p-methylphenyl group.

[A]

In the formulas (I) and (II), A represents an oxygen atom or a sulfur atom.

In the present invention, A is preferably an oxygen atom.

[$X^1$, m]

In the formulas (I) and (II), $X^1$ represents a halogeno group, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{1-6}$ alkoxy group, a substituted or unsubstituted $C_{2-6}$ alkenyloxy group, a substituted or unsubstituted $C_{2-6}$ alkynyloxy group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{3-8}$ cycloalkyl group, a substituted or unsubstituted $C_{6-10}$ aryl group, a substituted or unsubstituted $C_{6-10}$ aryloxy group, a substituted or unsubstituted 5- to 6-membered heteroaryl group, a substituted or unsubstituted 5- to 6-membered heteroaryloxy group, a group represented by $R^aR^bN$—, a group represented by $R^aR^bN$—CO—, a group represented by $R^cCO$—NH—, a pentafluorosulfanyl group, a nitro group or a cyano group; and m represents the number of $X^1$ groups and is any integer of 0 to 5. When m is 2 or more, $X^1$ groups may be the same or different from each other.

As the "halogeno group" represented by $X^1$, a fluoro group, a chloro group, a bromo group, an iodo group and the like can be mentioned.

The "$C_{1-6}$ alkyl group" represented by $X^1$ may be linear or branched. Examples of the "$C_{1-6}$ alkyl group" represented by $X^1$ include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group.

Examples of the "$C_{2-6}$ alkenyl group" represented by $X^1$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group and a 5-hexenyl group.

Examples of the "$C_{2-6}$ alkynyl group" represented by $X^1$ include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group and a 1,1-dimethyl-2-butynyl group.

Examples of the "$C_{1-6}$ alkoxy group" represented by $X^1$ include a methoxy group, an ethoxy group, an n-propoxy group, an n-butoxy group, an n-pentyloxy group, an n-hexyloxy group, an i-propoxy group, an i-butoxy group, an s-butoxy group, a t-butoxy group and an i-hexyloxy group.

Examples of the "$C_{2-6}$ alkenyloxy group" represented by $X^1$ include a vinyloxy group, an allyloxy group, a propenyloxy group and a butenyloxy group.

Examples of the "$C_{2-6}$ alkynyloxy group" represented by $X^1$ include an ethynyloxy group and a propargyloxy group.

Examples of the "$C_{1-6}$ alkylcarbonyl group" represented by $X^1$ include an acetyl group and a propionyl group.

Examples of the "$C_{1-6}$ alkoxycarbonyl group" represented by $X^1$ include a methoxycarbonyl group, an ethoxycarbonyl group, an n-propoxycarbonyl group, an i-propoxycarbonyl group and a t-butoxycarbonyl group.

Examples of the "$C_{1-6}$ alkylthio group" represented by $X^1$ include a methylthio group, an ethylthio group, an n-propylthio group, an n-butylthio group, an n-pentylthio group, an n-hexylthio group and an i-propylthio group.

Examples of the "$C^{1-6}$ alkylsulfinyl group" represented by $X^1$ include a methylsulfinyl group, an ethylsulfinyl group and a t-butylsulfinyl group.

Examples of the "$C_{1-6}$ alkylsulfonyl group" represented by $X^1$ include a methylsulfonyl group, an ethylsulfonyl group and a t-butylsulfonyl group.

As the substituent on the "$C_{1-6}$ alkyl group", "$C_{2-6}$ alkenyl group", "$C_{2-6}$ alkynyl group", "$C_{1-6}$ alkoxy group", "$C_{2-6}$ alkenyloxy group", "$C_{2-6}$ alkynyloxy group", "$C_{1-6}$ alkylcarbonyl group", "$C_{1-6}$ alkoxycarbonyl group", "$C_{1-6}$ alkylthio group", "$C_{1-6}$ alkylsulfinyl group" or "$C_{1-6}$ alkylsulfonyl group" represented by $X^1$, a halogeno group such as a fluoro group, a chloro group, a bromo group and an iodo group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; a $C_{6-10}$ aryl group such as a phenyl group and a naphthyl group; or a cyano group; is preferable.

Examples of the "$C_{3-8}$ cycloalkyl group" represented by $X^1$ include a cyclopropyl group, a cyclobutyl group, a cyclopentyl group, a cyclohexyl group and a cycloheptyl group.

Examples of the "$C_{6-10}$ aryl group" represented by $X^1$ include a phenyl group and a naphthyl group.

Examples of the "$C_{6-10}$ aryloxy group" represented by $X^1$ include a phenoxy group and a naphthoxy group.

The "5- to 6-membered heteroaryl group" represented by $X^1$ contains 1, 2, 3 or 4 hetero atoms selected from the group consisting of a nitrogen atom, an oxygen atom and a sulfur atom as constituent atoms of the ring. When there are two or more hetero atoms, they may be the same or different.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group and a tetrazolyl group, and examples of the 6-membered heteroaryl group include a pyridyl group, a pyrazinyl group, a pyrimidinyl group, a pyridazinyl group and a triazinyl group.

The "5- to 6-membered heteroaryloxy group" represented by $X^1$ has a structure in which a 5- or 6-membered heteroaryl group and an oxy group are bonded. Specific examples thereof include a thiazolyloxy group and a pyridyloxy group.

As the substituent on the "$C_{3-8}$ cycloalkyl group", "$C_{6-10}$ aryl group", "$C_{6-10}$ aryloxy group", "5- to 6-membered heteroaryl group", or "5- to 6-membered heteroaryloxy group" represented by $X^1$, a halogeno group such as a fluoro group, a chloro group, a bromo group and an iodo group; a $C_{1-6}$ alkyl group such as a methyl group, an ethyl group, an n-propyl group, an i-propyl group, an n-butyl group, an s-butyl group, an i-butyl group, a t-butyl group, an n-pentyl group and an n-hexyl group; a $C_{1-6}$ haloalkyl group such as a chloromethyl group, a chloroethyl group, a trifluoromethyl group, a 1,2-dichloro-n-propyl group and a 1-fluoro-n-butyl group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; or a cyano group; is preferable.

In the "group represented by $R^aR^bN$—" or "group represented by $R^aR^bN$—CO—" represented by $X^1$, $R^a$ represents a hydrogen atom, a substituted or unsubstituted $C_{1-6}$ alkyl group, or a substituted or unsubstituted $C_{6-10}$ aryl group, and $R^b$ represents a hydrogen atom, a substituted or unsubstituted $C_{1-6}$ alkyl group, or a substituted or unsubstituted $C_{6-10}$ aryl group.

The "$C_{1-6}$ alkyl group" represented by $R^a$ or $R^b$ may be linear or branched. Examples of the "$C_{1-6}$ alkyl group" represented by $R^a$ or $R^b$ include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group. As the substituent on the "$C_{1-6}$ alkyl group", a halogeno group such as a fluoro group, a chloro group, a bromo group and an iodo group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; a $C_{6-10}$ aryl group such as a phenyl group and a naphthyl group; or a cyano group; is preferable.

Examples of the "$C_{6-10}$ aryl group" represented by $R^a$ or $R^b$ include a phenyl group and a naphthyl group. As the substituent on the "$C^{6-10}$ aryl group", a halogeno group such as a fluoro group, a chloro group, a bromo group and an iodo group; a $C^{1-6}$ alkyl group such as a methyl group, an ethyl group, an n-propyl group, an i-propyl group, an n-butyl group, an s-butyl group, an i-butyl group, a t-butyl group, an n-pentyl group and an n-hexyl group; a $C_{1-6}$ haloalkyl group such as a chloromethyl group, a chloroethyl group, a trifluoromethyl group, a 1,2-dichloro-n-propyl group and a 1-fluoro-n-butyl group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C^{1-6}$ haloalkoxy group such as a 2-chloro-n-propoxy group, a 2,3-dichlorobutoxy group and a trifluoromethoxy group; or a cyano group; is preferable.

In the "group represented by $R^cCO$—NH—" represented by $X^1$, $R^c$ represents a hydrogen atom, a substituted or unsubstituted $C_{1-6}$ alkyl group, or a substituted or unsubstituted $C_{6-10}$ aryl group.

The "$C_{1-6}$ alkyl group" represented by $R^c$ may be linear or branched. Examples of the "$C_{1-6}$ alkyl group" represented by R include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group. As the substituent on the "$C_{1-6}$ alkyl group", a halogeno group such as a fluoro group, a chloro group, a bromo group and an iodo group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; a $C_{6-10}$ aryl group such as a phenyl group and a naphthyl group; or a cyano group; is preferable.

Examples of the "$C^{6-10}$ aryl group" represented by $R^c$ include a phenyl group and a naphthyl group. As the substituent on the "$C_{6-10}$ aryl group", a halogeno group such as a fluoro group, a chloro group, a bromo group and an iodo group; a $C_{1-6}$ alkyl group such as a methyl group, an ethyl group, an n-propyl group, an i-propyl group, an n-butyl group, an s-butyl group, an i-butyl group, a t-butyl group, an n-pentyl group and an n-hexyl group; a $C_{1-6}$ haloalkyl group such as a chloromethyl group, a chloroethyl group, a trifluoromethyl group, a 1,2-dichloro-n-propyl group and a 1-fluoro-n-butyl group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; or a cyano group; is preferable.

In the present invention, $X^1$ is preferably a halogeno group, a halogeno group-substituted or unsubstituted $C_{1-6}$ alkyl group, or a halogeno group-substituted or unsubstituted $C_{1-6}$ alkoxy group.

Examples of the "halogeno group-substituted $C_{1-6}$ alkyl group" represented by $X^1$ include a difluoromethyl group, a trifluoromethyl group, a 2,2,2-trifluoroethyl group and a 2,2,2,1,1-pentafluoroethyl group.

Examples of the "halogeno group-substituted $C_{1-6}$ alkoxy group" represented by $X^1$ include a difluoromethoxy group, a trifluoromethoxy group, a 2,2-difluoroethoxy group, a 2,2,2-trifluoroethoxy group, a 2,2,1,1-tetrafluoroethoxy group and a 2,2,2,1,1-pentafluoroethoxy group.

[Z]

Z represents a group represented by the following formula (Z-1) or formula (Z-2).

(Chemical Formula 12)

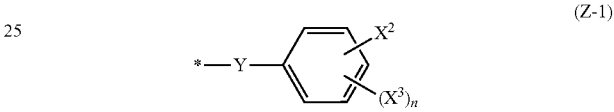

(Z-1)

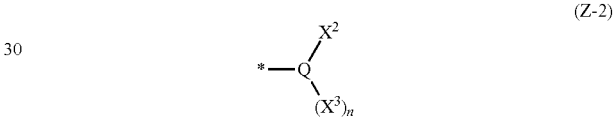

(Z-2)

A bond marked with a symbol * means a bond with a carbonyl group or a thiocarbonyl group in a pyridinium salt.

[Y]

Y represents a substituted or unsubstituted $C_{2-6}$ alkenylene group.

Examples of the "$C_{2-6}$ alkenylene group" represented by Y include a vinylene group (—CH=CH—), a divinylene group (—CH=CH—CH=CH—), and a propenylene group (—CH=CH—$CH_2$—, —$CH_2$—CH=CH—).

As the substituent on the "$C_{2-6}$ alkenylene group" represented by Y, a halogeno group such as a fluoro group, a chloro group, a bromo group and an iodo group; a $C_{1-6}$ alkyl group such as a methyl group, an ethyl group, an n-propyl group, an i-propyl group, an n-butyl group, an s-butyl group, an i-butyl group and a t-butyl group; a $C_{2-6}$ alkynyl group such as an ethynyl group; a $C_{1-6}$ haloalkyl group such as a chloromethyl group, a chloroethyl group, a trifluoromethyl group, a 1,2-dichloro-n-propyl group and a 1-fluoro-n-butyl group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; a $C_{1-6}$ alkoxy $C_{1-6}$ alkyl group such as a methoxymethyl group; a $C_{1-6}$ alkylthio group such as a methylthio group, an ethylthio group, an n-propylthio group, an i-propylthio group, an n-butylthio group, an i-butylthio group, an s-butylthio group and a t-butylthio group; a $C_{1-6}$ alkylsulfinyl group such as a methylsulfinyl group, an ethylsulfinyl group and a t-butylsulfinyl group; or a $C_{1-6}$ alkylsulfonyl group such as a methylsulfonyl group, an ethylsulfonyl group and a t-butylsulfonyl group; is preferable.

[Q]

Q represents a naphthalene ring or a 6- to 10-membered heteroaryl ring.

Examples of the 6-membered heteroaryl ring include a pyridine ring, a pyrazine ring, a pyrimidine ring, a pyridazine ring, and a triazine ring.

Examples of the 9-membered heteroaryl ring include an indole ring, a benzofuran ring, a benzothiophene ring, an indazole ring, a benzimidazole ring, a benzoxazole ring, a benzothiazole ring, a benzisoxazole ring, and a benzisothiazole ring.

Examples of the 10-membered heteroaryl ring include a quinoline ring, an isoquinoline ring, a cinnoline ring, a phthalazine ring, a quinazoline ring, and a quinoxaline ring.

[$X^2$]

$X^2$ represents a substituted or unsubstituted $C_{1-6}$ alkyl group, a substituted or unsubstituted $C_{2-6}$ alkenyl group, a substituted or unsubstituted $C_{2-6}$ alkynyl group, a hydroxyl group, a substituted or unsubstituted $C_{1-6}$ alkoxy group, a substituted or unsubstituted $C_{2-6}$ alkenyloxy group, a substituted or unsubstituted $C_{2-6}$ alkynyloxy group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{3-8}$ cycloalkyl group, a substituted or unsubstituted $C_{6-10}$ aryloxy group, a substituted or unsubstituted 5- to 6-membered heteroaryloxy group, a group represented by $R^{a1}R^{b1}N-$, a group represented by $R^{a1}R^{b1}N-CO-$, a group represented by $R^{c1}CO-NH-$, a group represented by $R^{d1}O-N=CR^{f1}-$, a pentafluorosulfanyl group, a nitro group or a cyano group.

In the "group represented by $R^{a1}R^{b1}N-$" or "group represented by $R^{a1}R^{b1}N-CO-$" represented by $X^2$, $R^{a1}$ represents a hydrogen atom, a substituted or unsubstituted $C_{1-6}$ alkyl group, or a substituted or unsubstituted $C_{6-10}$ aryl group, and $R^{b1}$ represents a hydrogen atom, a substituted or unsubstituted $C_{1-6}$ alkyl group, or a substituted or unsubstituted $C_{6-10}$ aryl group.

The "$C_{1-6}$ alkyl group" represented by $R^{a1}$ or $R^{b1}$ may be linear or branched. Examples of the "$C_{1-6}$ alkyl group" represented by $R^{a1}$ or $R^{b1}$ include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group. As the substituent on the "$C_{1-6}$ alkyl group", a halogeno group such as a fluoro group, a chloro group, a bromo group and an iodo group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; a $C_{6-10}$ aryl group such as a phenyl group and a naphthyl group; or a cyano group; is preferable.

Examples of the "$C_{6-10}$ aryl group" represented by $R^{a1}$ or $R^{b1}$ include a phenyl group and a naphthyl group. As the substituent on the "$C_{6-10}$ aryl group", a halogeno group such as a fluoro group, a chloro group, a bromo group and an iodo group; a $C_{1-6}$ alkyl group such as a methyl group, an ethyl group, an n-propyl group, an i-propyl group, an n-butyl group, an s-butyl group, an i-butyl group, a t-butyl group, an n-pentyl group and an n-hexyl group; a $C_{1-6}$ haloalkyl group such as a chloromethyl group, a chloroethyl group, a trifluoromethyl group, a 1,2-dichloro-n-propyl group and a 1-fluoro-n-butyl group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; or a cyano group; is preferable.

In the "group represented by $R^{c1}CO-NH-$" represented by $X^2$, $R^{c1}$ represents a hydrogen atom, a substituted or unsubstituted $C_{1-6}$ alkyl group, or a substituted or unsubstituted $C_{6-10}$ aryl group.

The "$C_{1-6}$ alkyl group" represented by $R^{c1}$ may be linear or branched. Examples of the "$C^{1-6}$ alkyl group" represented by $R^{c1}$ include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group. As the substituent on the "$C_{1-6}$ alkyl group", a halogeno group such as a fluoro group, a chloro group, a bromo group and an iodo group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; a $C_{6-10}$ aryl group such as a phenyl group and a naphthyl group; or a cyano group; is preferable.

Examples of the "$C_{6-10}$ aryl group" represented by $R^{c1}$ include a phenyl group and a naphthyl group. As the substituent on the "$C_{6-10}$ aryl group", a halogeno group such as a fluoro group, a chloro group, a bromo group and an iodo group; a $C_{1-6}$ alkyl group such as a methyl group, an ethyl group, an n-propyl group, an i-propyl group, an n-butyl group, an s-butyl group, an i-butyl group, a t-butyl group, an n-pentyl group and an n-hexyl group; a $C_{1-6}$ haloalkyl group such as a chloromethyl group, a chloroethyl group, a trifluoromethyl group, a 1,2-dichloro-n-propyl group and a 1-fluoro-n-butyl group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; or a cyano group; is preferable.

In the "group represented by $R^{d1}O-N=CR^{f1}-$" represented by X2, $R^{d1}$ represents a hydrogen atom or a substituted or unsubstituted $C_{1-6}$ alkyl group, and $R^{f1}$ represents a hydrogen atom or a substituted or unsubstituted $C_{1-6}$ alkyl group.

The "$C_{1-6}$ alkyl groups" represented by $R^{d1}$ and $R^{f1}$ may be linear or branched. Examples of the "$C_{1-6}$ alkyl groups" represented by $R^{d1}$ and $R^{f1}$ include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group.

As the substituent on the "$C_{1-6}$ alkyl group", a halogeno group such as a fluoro group, a chloro group, a bromo group and an iodo group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; a $C_{6-10}$ aryl group such as a phenyl group and a naphthyl group; or a cyano group; is preferable.

Examples of the group represented by $R^{d1}O-N=CR^{f1}-$ include a (hydroxyimino) methyl group, a (methoxyimino) methyl group, an (ethoxyimino) methyl group, a (methoxyimino) ethyl group, and an (ethoxyimino) ethyl group.

As the substituent on the "$C_{1-6}$ alkyl group", a halogeno group is particularly preferable.

Specific examples of other groups represented by $X^2$ include the same as those exemplified for $X^1$.

In the present invention, $X^2$ is preferably a halogeno group-substituted or unsubstituted $C_{1-6}$ alkyl group, or a halogeno group-substituted or unsubstituted $C_{1-6}$ alkoxy group.

Examples of the "halogeno group-substituted $C_{1-6}$ alkyl group" represented by $X^2$ include a difluoromethyl group, a trifluoromethyl group, a 2,2,2-trifluoroethyl group and a 2,2,2,1,1-pentafluoroethyl group.

Examples of the "halogeno group-substituted $C_{1-6}$ alkoxy group" represented by $X^2$ include a difluoromethoxy group, a trifluoromethoxy group, a 2,2-difluoroethoxy group, a 2,2,2-trifluoroethoxy group, a 2,2,1,1-tetrafluoroethoxy group and a 2,2,2,1,1-pentafluoroethoxy group.

[$X^3$, n]

$X^3$ represents a halogeno group, a substituted or unsubstituted $C_{1-6}$ alkyl group, a hydroxyl group, a substituted or unsubstituted $C_{1-6}$ alkoxy group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a pentafluorosulfanyl group, a nitro group, or a cyano group; and n represents the number of $X^3$ groups and is any integer of 0 to 4.

Specific examples of these groups represented by $X^3$ include the same as those exemplified for $X^1$. When n is 2 or more, $X^3$ groups may be the same or different from each other.

In the present invention, when Z is a group represented by a formula (Z-1), it can be represented by the following formula (I-1) or formula (II-1).

[Chemical Formula 13]

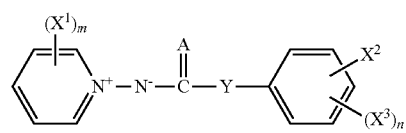

(I-1)

[Chemical Formula 14]

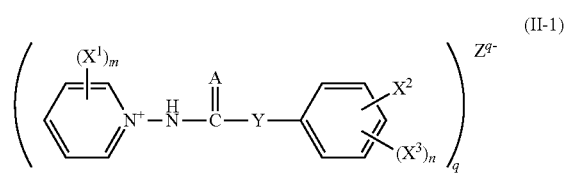

(II-1)

In the formula (I-1) and formula (II-1), A, $X^1$, m, Y, $X^2$, $X^3$, n, $Z^{q-}$, and q have the same meanings as those defined in the formula (I) or formula (II).

In the present invention, when Z is a group represented by a formula (Z-2), it can be represented by the following formula (I-2) or formula (II-2).

[Chemical Formula 15]

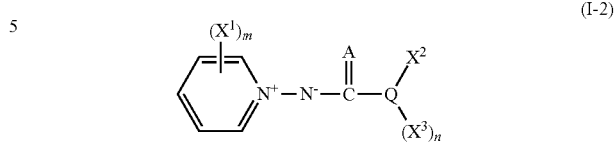

(I-2)

[Chemical Formula 16]

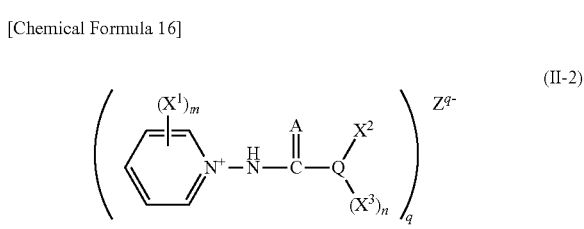

(II-2)

In the formulas (I-2) and (II-2), A, $X^1$, m, Q, $X^2$, $X^3$, n, $Z^{q-}$, and q have the same meanings as those defined in the formula (I) or formula (II).

The pyridinium salt of the present invention is not particularly limited by the production method thereof. For example, the pyridinium salt of the present invention (hereinafter sometimes referred to as the "compound of the present invention") can be obtained using a known reaction described in Examples and the like.

The compound of the present invention can also be produced, for example, by the following method.

[Production of N-Aminopyridinium Salt]

[Chemical Formula 17]

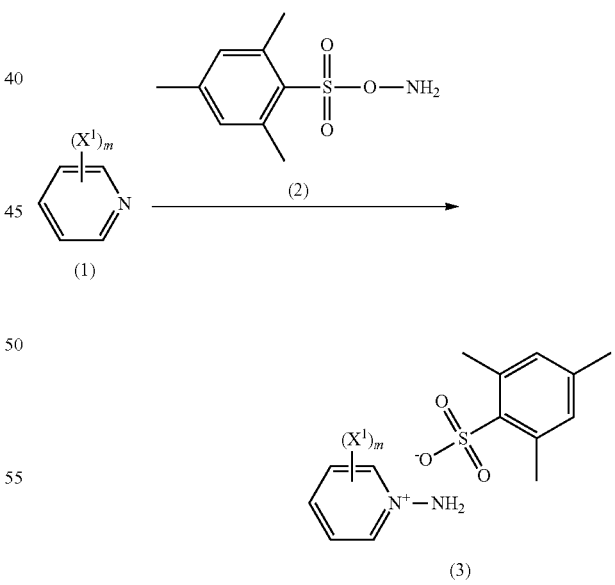

An N-aminopyridinium salt (3) can be prepared by reacting a pyridine compound (1) with O-(mesitylsulfonyl) hydroxylamine (2).

In addition to O-(mesitylsulfonyl) hydroxylamine, hydroxylamine-O-sulfonic acid, O-(diphenylphosphinyl) hydroxylamine and the like can also be used.

[Chemical Formula 18]

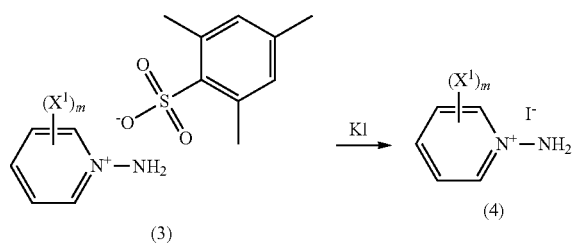

The N-aminopyridinium salt (3) can be used as it is for next condensation with a carboxylic acid compound (5), but can be subjected to salt exchange to form an iodide salt and used as an N-aminopyridinium salt (4), when it is necessary to consider the substrate stability.

It should be noted that $X^1$ and m in a reaction formula have the same meanings as those defined in the above formulas (I) and (II).

[Condensation Reaction]

[Chemical Formula 19]

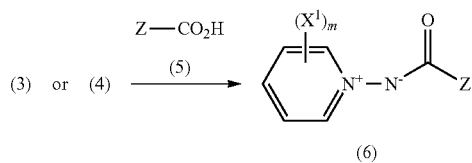

A compound (6) of the present invention can be produced by condensation of the N-aminopyridinium salt (3) or (4) with the carboxylic acid compound (5) in the presence of a condensing agent used for amide synthesis.

Examples of the condensing agent include dicyclohexylcarbodiimide (DCC), diisopropylcarbodiimide (DIC) and 1-ethyl-3-(3-dimethylaminopropyl)-carbodiimide (EDI).

It should be noted that Z in a reaction formula has the same meanings as those defined in the above formulas (I) and (II). Furthermore, the substituent in Z can be appropriately converted after this condensation reaction.

Further, when producing a compound in which A in the above formulas (I) and (II) is sulfur, it can be produced by using a dithiocarboxylic acid ester (7) instead of the carboxylic acid compound (5).

[Chemical Formula 20]

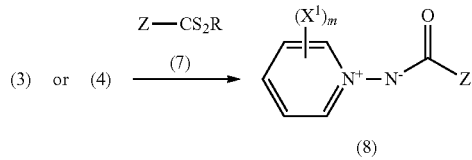

In a condensation reaction with the dithiocarboxylic acid ester (7), it is preferable to use a base such as potassium carbonate and sodium ethoxide.

It should be noted that R in a reaction formula represents a $C_{1-6}$ alkyl group such as a methyl group and an ethyl group.

The compound of the present invention is excellent in the effect of controlling harmful organisms such as various agricultural pests affecting the growth of plants, and mites and ticks.

In addition, the compound of the present invention is a highly safe substance because it has less phytotoxicity to crops and has low toxicity to fish and warm-blooded animals. Therefore, it is useful as an active ingredient of an insecticide or acaricide.

Furthermore, in recent years, resistance to various existing drugs has developed in a number of insect pests such as diamondback moths, planthoppers, leafhoppers and aphids, causing problems of insufficient efficacy of these drugs, and drugs that are effective even against resistant strains of insect pests have been desired. The compound of the present invention exhibits an excellent controlling effect not only on susceptible strains but also on various resistant strains of insect pests and acaricide-resistant strains of mites and ticks.

The compound of the present invention is excellent in the effect of controlling ectoparasites and endoparasites that are harmful to humans and animals. In addition, it is a highly safe substance because it has low toxicity to fish and warm-blooded animals. Therefore, it is useful as an active ingredient of an agent for controlling ectoparasites and endoparasites.

In addition, the compound of the present invention shows efficacy in all developmental stages of organisms to be controlled, and shows an excellent control effect, for example, on eggs, nymphs, larvae, pupae and adults of mites and ticks, insects and the like.

[Pest Control Agent, Insecticidal or Acaricidal Agent]

The pest control agent or the insecticidal or acaricidal agent of the present invention contains at least one selected from the compounds of the present invention as an active ingredient. The amount of the compound of the present invention contained in the pest control agent or the insecticidal or acaricidal agent of the present invention is not particularly limited as long as it shows the effect of controlling harmful organisms, agricultural pests or mites and ticks, but it is usually preferably within the range of 0.01 to 90 parts by mass, and more preferably within the range of 0.1 to 50 parts by mass, with respect to 100 parts by mass of the control agent, insecticide or acaricide of the present invention.

The pest control agent or the insecticidal or acaricidal agent of the present invention is preferably used for plants such as grains; vegetables; root vegetables; potatoes; flowers and ornamental plants; fruit trees; foliage plants and trees of tea, coffee, cacao and the like; pasture grasses; turf grasses; and cotton.

In application to plants, the pest control agent or the insecticidal or acaricidal agent of the present invention may be used to any portions of leaves, stems, stalks, flowers, buds, fruits, seeds, sprouts, roots, tubers, tuberous roots, shoots, cuttings and the like.

Further, the pest control agent or the insecticidal or acaricidal agent of the present invention is not particularly limited by the species of the plant to be applied. Examples of the plant species include an original species, a variant species, an improved variety, a cultivar, a mutant, a hybrid and a genetically modified organism (GMO).

The pest control agent of the present invention can be used for seed treatment, foliage application, soil application, water surface application and the like, in order to control various agricultural pests and mites and ticks.

Specific examples of various agricultural pests and mites and ticks which can be controlled by the pest control agent of the present invention are shown below.

(1) Butterflies or Moths of the Order Lepidoptera (a) Moths of the family Arctiidae such as *Hyphantria cunea* and *Lemyra imparilis*;

(b) moths of the family Bucculatricidae such as *Bucculatrix pyrivorella*;

(c) moths of the family Carposinidae such as *Carposina sasakii*;

(d) moths of the family Crambidae, for example, species belonging to the genus *Diaphania* (*Diaphania* spp.) such as *Diaphania indica* and *Diaphania nitidalis*; for example, species belonging to the genus *Ostrinia* (*Ostrinia* spp.) such as *Ostrinia furnacalis*, *Ostrinia nubilalis* and *Ostrinia scapulalis*; and others such as *Chilo suppressalis*, *Cnaphalocrocis medinalis*, *Conogethes punctiferalis*, *Diatraea grandiosella*, *Glyphodes pyloalis*, *Hellula undalis* and *Parapediasia teterrella*;

(e) moths of the family Gelechiidae such as *Helcystogramma triannulella*, *Pectinophora gossypiella*, *Phthorimaea operculella* and *Sitotroga cerealella*;

(f) moths of the family Geometridae such as *Ascotis selenaria*;

(g) moths of the family Gracillariidae such as *Caloptilia theivora*, *Phyllocnistis citrella* and *Phyllonorycter ringoniella*;

(h) butterflies of the family Hesperiidae such as *Parnara guttata*;

(i) moths of the family Lasiocampidae such as *Malacosoma neustria*;

(j) moths of the family Lymantriidae, for example, species belonging to the genus *Lymantria* (*Lymantria* spp.) such as *Lymantria dispar* and *Lymantria monacha*; and others such as *Euproctis pseudoconspersa* and *Orgyia thyellina*;

(k) moths of the family Lyonetiidae, for example, species belonging to the genus *Lyonetia* (*Lyonetia* spp.) such as *Lyonetia clerkella* and *Lyonetia prunifoliella malinella*;

(l) moths of the family Noctuidae, for example, species belonging to the genus *Spodoptera* (*Spodoptera* spp.) such as *Spodoptera depravata*, *Spodoptera eridania*, *Spodoptera exigua*, *Spodoptera frugiperda*, *Spodoptera littoralis* and *Spodoptera litura*; for example, species belonging to the genus *Autographa* (*Autographa* spp.) such as *Autographa gamma* and *Autographa nigrisigna*; for example, species belonging to the genus *Agrotis* (*Agrotis* spp.) such as *Agrotis ipsilon* and *Agrotis segetum*; for example, species belonging to the genus *Helicoverpa* (*Helicoverpa* spp.) such as *Helicoverpa armigera*, *Helicoverpa assulta* and *Helicoverpa zea*; for example, species belonging to the genus *Heliothis* (*Heliothis* spp.) such as *Heliothis armigera* and *Heliothis virescens*; and others such as *Aedia leucomelas*, *Ctenoplusia agnata*, *Eudocima tyrannus*, *Mamestra brassicae*, *Mythimna separata*, *Naranga aenescens*, *Panolis japonica*, *Peridroma saucia*, *Pseudoplusia includens* and *Trichoplusia ni*;

(m) moths of the family Nolidae such as *Earias insulana*;

(n) butterflies of the family Pieridae, for example, species belonging to the genus *Pieris* (*Pieris* spp.) such as *Pieris brassicae* and *Pieris rapae crucivora*;

(o) moths of the family Plutellidae, for example, species belonging to the genus *Acrolepiopsis* (*Acrolepiopsis* spp.) such as *Acrolepiopsis sapporensis* and *Acrolepiopsis suzukiella*; and others such as *Plutella xylostella*;

(p) moths of the family Pyralidae such as *Cadra cautella*, *Elasmopalpus lignosellus*, *Etiella zinckenella* and *Galleria mellonella*;

(q) moths of the family Sphingidae, for example, species belonging to the genus *Manduca* (*Manduca* spp.) such as *Manduca quinquemaculata* and *Manduca sexta*;

(r) moths of the family Stathmopodidae such as *Stathmopoda masinissa*;

(s) moths of the family Tineidae such as *Tinea translucens*;

(t) moths of the family Tortricidae, for example, species belonging to the genus *Adoxophyes* (*Adoxophyes* spp.) such as *Adoxophyes honmai* and *Adoxophyes orana*; for example, species belonging to the genus *Archips* (*Archips* spp.) such as *Archips breviplicanus* and *Archips fuscocupreanus*; and others such as *Choristoneura fumiferana*, *Cydia pomonella*, *Eupoecilia ambiguella*, *Grapholitha molesta*, *Homona magnanima*, *Leguminivora glycinivorella*, *Lobesia botrana*, *Matsumuraeses phaseoli*, *Pandemis heparana* and *Sparganothis pilleriana*; and (u) moths of the family Yponomeutidae such as *Argyresthia conjugella*.

(2) Insect Pests of the Order Thysanoptera (a) pests of the family Phlaeothripidae such as *Ponticulothrips diospyrosi*; and (b) pests of the family Thripidae, for example, species belonging to the genus *Frankliniella* (*Frankliniella* spp.) such as *Frankliniella intonsa* and *Frankliniella occidentalis*; for example, species belonging to the genus *Thrips* (*Thrips* spp.) such as *Thrips palmi* and *Thrips tabaci*; and others such as *Heliothrips haemorrhoidalis* and *Scirtothrips dorsalis*.

(3) Insect Pests of the Order Hemiptera (A) Archaeorrhyncha (a) pests of the family Delphacidae such as *Laodelphax striatella*, *Nilaparvata lugens*, *Perkinsiella saccharicida* and *Sogatella furcifera*.

(B) Clypeorrhyncha (a) pests of the family Cicadellidae, for example, species belonging to the genus *Empoasca* (*Empoasca* spp.) such as *Empoasca fabae*, *Empoasca nipponica*, *Empoasca onukii* and *Empoasca sakaii*; and others such as *Arboridia apicalis*, *Balclutha saltuella*, *Epiacanthus stramineus*, *Macrosteles striifrons* and *Nephotettix cincticeps*.

(C) Heteroptera (a) pests of the family Alydidae such as *Riptortus clavatus*;

(b) pests of the family Coreidae such as *Cletus punctiger* and *Leptocorisa chinensis*;

(c) pests of the family Lygaeidae such as *Blissus leucopterus*, *Cavelerius saccharivorus* and *Togo hemipterus*;

(d) pests of the family Miridae such as Halticus *insularis*, *Lygus lineolaris*, *Psuedatomoscelis seriatus*, *Stenodema sibiricum*, *Stenotus rubrovittatus* and *Trigonotylus caelestialium*;

(e) pests of the family Pentatomidae, for example, species belonging to the genus *Nezara* (*Nezara* spp.) such as *Nezara antennata* and *Nezara viridula*; for example, species belonging to the genus *Eysarcoris* (*Eysarcoris* spp.) such as *Eysarcoris aeneus*, *Eysarcoris lewisi* and *Eysarcoris ventralis*; and others such as *Dolycoris baccarum*, *Eurydema rugosum*, *Glaucias subpunctatus*, *Halyomorpha halys*, *Piezodorus hybneri*, *Plautia crossota* and *Scotinophora lurida*;

(f) pests of the family Pyrrhocoridae such as *Dysdercus cingulatus*;

(g) pests of the family Rhopalidae such as *Rhopalus msculatus*;

(h) pests of the family Scutelleridae such as *Eurygaster integriceps*; and (i) pests of the family Tingidae such as *Stephanitis nashi*.

(D) Sternorrhyncha (a) pests of the family Adelgidae such as *Adelges laricis*;

(b) pests of the family Aleyrodidae, for example, species belonging to the genus *Bemisia* (*Bemisia* spp.) such as *Bemisia argentifolii* and *Bemisia tabaci*; and others such as *Aleurocanthus spiniferus*, *Dialeurodes citri* and *Trialeurodes vaporariorum*;

(c) pests of the family Aphididae, for example, species belonging to the genus *Aphis* (*Aphis* spp.) such as *Aphis craccivora*, *Aphis fabae*, *Aphis forbesi*, *Aphis gossypii*, *Aphis pomi*, *Aphis sambuci* and *Aphis spiraecola*; for example, species belonging to the genus *Rhopalosiphum* (*Rhopalosiphum* spp.) such as *Rhopalosiphum maidis* and *Rhopalosiphum padi*; for example, species belonging to the genus *Dysaphis* (*Dysaphis* spp.) such as *Dysaphis plantaginea* and *Dysaphis radicola*; for example, species belonging to the genus *Macrosiphum* (*Macrosiphum* spp.) such as *Macrosiphum avenae* and *Macrosiphum euphorbiae*; for example, species belonging to the genus *Myzus* (*Myzus* spp.) such as *Myzus cerasi*, *Myzus persicae* and *Myzus varians*; and others such as *Acyrthosiphon pisum*, *Aulacorthum solani*, *Brachycaudus helichrysi*, *Brevicoryne brassicae*, *Chaetosiphon fragaefolii*, *Hyalopterus pruni*, *Hyperomyzus lactucae*, *Lipaphis erysimi*, *Megoura viciae*, *Metopolophium dirhodum*, *Nasonovia ribis-nigri*, *Phorodon humuli*, *Schizaphis graminum*, *Sitobion avenae* and *Toxoptera aurantii*;

(d) pests of the family Coccidae, for example, species belonging to the genus *Ceroplastes* (*Ceroplastes* spp.) such as *Ceroplastes ceriferus* and *Ceroplastes rubens*;

(e) pests of the family Diaspididae, for example, species belonging to the genus *Pseudaulacaspis* (*Pseudaulacaspis* spp.) such as *Pseudaulacaspis pentagona* and *Pseudaulacaspis prunicola*; for example, species belonging to the genus *Unaspis* (*Unaspis* spp.) such as *Unaspis euonymi* and *Unaspis yanonensis*; and others such as *Aonidiella aurantii*, *Comstockaspis perniciosa*, *Fiorinia theae* and *Pseudaonidia paeoniae*;

(f) pests of the family Margarodidae such as *Drosicha corpulenta* and *Icerya purchasi*;

(g) pests of the family Phylloxeridae such as *Viteus vitifolii*;

(h) pests of the family Pseudococcidae, for example, species belonging to the genus *Planococcus* (*Planococcus* spp.) such as *Planococcus citri* and *Planococcus kraunhiae*; and others such as *Phenacoccus solani* and *Pseudococcus comstocki*; and (i) pests of the family Psyllidae, for example, species belonging to the genus *Psylla* (*Psylla* spp.) such as *Psylla mali* and *Psylla pyrisuga*; and others such as *Diaphorina citri*.

(4) Insect Pests of the Suborder Polyphaga (a) pests of the family Anobiidae such as *Lasioderma serricorne*;

(b) pests of the family Attelabidae such as *Byctiscus betulae* and *Rhynchites heros*;

(c) pests of the family Bostrichidae such as *Lyctus brunneus*;

(d) pests of the family Brentidae such as *Cylas formicarius*;

(e) pests of the family Buprestidae such as *Agrilus sinuatus*;

(f) pests of the family Cerambycidae such as *Anoplophora malasiaca*, *Monochamus alternatus*, *Psacothea hilaris* and *Xylotrechus pyrrhoderus*;

(g) pests of the family Chrysomelidae, for example, species belonging to the genus *Bruchus* (*Bruchus* spp.) such as *Bruchus pisorum* and *Bruchus rufimanus*; for example, species belonging to the genus *Diabrotica* (*Diabrotica* spp.) such as *Diabrotica barberi*, *Diabrotica* undecimpunctata and *Diabrotica virgifera*; for example, species belonging to the genus *Phyllotreta* (*Phyllotreta* spp.) such as *Phyllotreta nemorum* and *Phyllotreta striolata*; and others such as *Aulacophora femoralis*, *Callosobruchus chinensis*, *Cassida nebulosa*, *Chaetocnema concinna*, *Leptinotarsa decemlineata*, *Oulema oryzae* and *Psylliodes angusticollis*;

(h) pests of the family Coccinellidae, for example, species belonging to the genus *Epilachna* (*Epilachna* spp.) such as *Epilachna varivestis* and *Epilachna vigintioctopunctata*;

(i) pests of the family Curculionidae, for example, species belonging to the genus *Anthonomus* (*Anthonomus* spp.) such as *Anthonomus grandis* and *Anthonomus pomorum*; for example, species belonging to the genus *Sitophilus* (*Sitophilus* spp.) such as *Sitophilus granarius* and *Sitophilus zeamais*; and others such as *Echinoenemus squameus*, *Euscepes postfasciatus*, *Hylobius abietis*, *Hypera postica*, *Lissohoptrus oryzophilus*, *Otiorhynchus sulcatus*, *Sitona lineatus* and *Sphenophorus venatus*;

(j) pests of the family Elateridae, for example, species belonging to the genus *Melanotus* (*Melanotus* spp.) such as *Melanotus fortnumi* and *Melanotus tamsuyensis*;

(k) pests of the family Nitidulidae such as *Epuraea domina*;

(l) pests of the family Scarabaeidae, for example, species belonging to the genus *Anomala* (*Anomala* spp.) such as *Anomala cuprea* and *Anomala rufocuprea*; and others such as *Cetonia aurata*, *Gametis jucunda*, *Heptophylla picea*, *Melolontha melolontha* and *Popillia japonica*;

(m) pests of the family Scolytidae such as *Ips typographus*;

(n) pests of the family Staphylinidae such as *Paederus fuscipes*;

(o) pests of the family Tenebrionidae such as *Tenebrio molitor* and *Tribolium castaneum*; and (p) pests of the family Trogossitidae such as *Tenebroides mauritanicus*.

(5) Insect Pests of the Order Diptera (A) Brachycera (a) pests of the family Agromyzidae, for example, species belonging to the genus *Liriomyza* (*Liriomyza* spp.) such as *Liriomyza bryoniae*, *Liriomyza chinensis*, *Liriomyza sativae* and *Liriomyza trifolii*; and others such as *Chromatomyia horticola* and *Agromyza oryzae*;

(b) pests of the family Anthomyiidae, for example, species belonging to the genus *Delia* (*Delia* spp.) such as *Delia platura* and *Delia radicum*; and others such as *Pegomya cunicularia*;

(c) pests of the family Drosophilidae, for example, species belonging to the genus *Drosophila* (*Drosophila* spp.) such as *Drosophila melanogaster* and *Drosophila suzukii*;

(d) pests of the family Ephydridae such as *Hydrellia griseola*;

(e) pests of the family Psilidae such as *Psila rosae*; and (f) pests of the family Tephritidae, for example, species belonging to the genus *Bactrocera* (*Bactrocera* spp.) such as *Bactrocera cucurbitae* and *Bactrocera dorsalis*; for example, species belonging to the genus *Rhagoletis* (*Rhagoletis* spp.) such as *Rhagoletis cerasi* and *Rhagoletis pomonella*; and others such as *Ceratitis capitata* and *Dacus oleae*.

(B) Nematocera (a) pests of the family Cecidomyiidae such as *Asphondylia yushimai*, *Contarinia sorghicola*, *Mayetiola destructor* and *Sitodiplosis mosellana*.

(6) Insect Pests of the Order Orthoptera (a) pests of the family Acrididae, for example, species belonging to the genus *Schistocerca* (*Schistocerca* spp.) such as *Schistocerca americana* and *Schistocerca gregaria*; and others such as *Chortoicetes terminifera, Dociostaurus maroccanus, Locusta migratoria, Locustana pardalina, Nomadacris septemfasciata* and *Oxya yezoensis;*

(b) pests of the family Gryllidae such as *Acheta domestica* and *Teleogryllus emma;*

(c) pests of the family Gryllotalpidae such as *Gryllotalpa orientalis*; and (d) pests of the family Tettigoniidae such as *Tachycines asynamorus.*

(7) Acari (A) Acaridida of the Order Astigmata (a) mites and ticks of the family Acaridae, for example, species belonging to the genus *Rhizoglyphus* (*Rhizoglyphus* spp.) such as *Rhizoglyphus echinopus* and *Rhizoglyphus robini*; for example, species belonging to the genus *Tyrophagus* (*Tyrophagus* spp.) such as *Tyrophagus neiswanderi, Tyrophagus perniciosus, Tyrophagus putrescentiae* and *Tyrophagus similis*; and others such as *Acarus siro, Aleuroglyphus ovatus* and *Mycetoglyphus fungivorus;*

(B) Actinedida of the Order Prostigmata (a) mites and ticks of the family Tetranychidae, for example, species belonging to the genus *Bryobia* (*Bryobia* spp.) such as *Bryobia praetiosa* and *Bryobia rubrioculus*; for example, species belonging to the genus *Eotetranychus* (*Eotetranychus* spp.) such as *Eotetranychus asiaticus, Eotetranychus boreus, Eotetranychus celtis, Eotetranychus geniculatus, Eotetranychus kankitus, Eotetranychus pruni, Eotetranychus shii, Eotetranychus smithi, Eotetranychus suginamensis* and *Eotetranychus uncatus*; for example, species belonging to the genus *Oligonychus* (*Oligonychus* spp.) such as *Oligonychus hondoensis, Oligonychus ilicis, Oligonychus karamatus, Oligonychus mangiferus, Oligonychus orthius, Oligonychus perseae, Oligonychus pustulosus, Oligonychus shinkajii* and *Oligonychus ununguis*; for example, species belonging to the genus *Panonychus* (*Panonychus* spp.) such as *Panonychus citri, Panonychus mori* and *Panonychus ulmi*; for example, species belonging to the genus *Tetranychus* (*Tetranychus* spp.) such as *Tetranychus cinnabarinus, Tetranychus evansi, Tetranychus kanzawai, Tetranychus ludeni, Tetranychus quercivorus, Tetranychus phaselus, Tetranychus urticae* and *Tetranychus viennensis*; for example, species belonging to the genus *Aponychus* (*Aponychus* spp.) such as *Aponychus corpuzae* and *Aponychus firmianae*; for example, species belonging to the genus *Sasanychus* (*Sasanychus* spp.) such as *Sasanychus akitanus* and *Sasanychus pusillus*; for example, species belonging to the genus *Shizotetranychus* (*Shizotetranychus* spp.) such as *Shizotetranychus celarius, Shizotetranychus longus, Shizotetranychus miscanthi, Shizotetranychus recki* and *Shizotetranychus schizopus*; and others such as *Tetranychina harti, Tuckerella pavoniformis* and *Yezonychus sapporensis;*

(b) mites and ticks of the family Tenuipalpidae, for example, species belonging to the genus *Brevipalpus* (*Brevipalpus* spp.) such as *Brevipalpus lewisi, Brevipalpus obovatus, Brevipalpus phoenicis, Brevipalpus russulus* and *Brevipalpus californicus*; for example, species belonging to the genus *Tenuipalpus* (*Tenuipalpus* spp.) such as *Tenuipalpus pacificus* and *Tenuipalpus zhizhilashviliae*; and others such as *Dolichotetranychus floridanus;*

(c) mites and ticks of the family Eriophyidae, for example, species belonging to the genus *Aceria* (*Aceria* spp.) such as *Aceria diospyri, Aceria ficus, Aceria japonica, Aceria kuko, Aceria paradianthi, Aceria tiyingi, Aceria tulipae* and *Aceria zoysiea*; for example, species belonging to the genus *Eriophyes* (*Eriophyes* spp.) such as *Eriophyes chibaensis* and *Eriophyes emarginatae*; for example, species belonging to the genus *Aculops* (*Aculops* spp.) such as *Aculops lycopersici* and *Aculops pelekassi*; for example, species belonging to the genus *Aculus* (*Aculus* spp.) such as *Aculus fockeui* and *Aculus schlechtendali*; and others such as *Acaphylla theavagrans, Calacarus carinatus, Colomerus vitis, Calepitrimerus vitis, Epitrimerus pyri, Paraphytoptus kikus, Paracalacarus podocarpi* and *Phyllocotruta citri;*

(d) mites and ticks of the family Transonemidae, for example, species belonging to the genus *Tarsonemus* (*Tarsonemus* spp.) such as *Tarsonemus bilobatus* and *Tarsonemus waitei*; and others such as *Phytonemus pallidus* and *Polyphagotarsonemus latus*; and (e) mites and ticks of the family Penthaleidae, for example, species belonging to the genus *Penthaleus* (*Penthaleus* spp.) such as *Penthaleus erythrocephalus* and *Penthaleus major.*

The pest control agent of the present invention may be mixed with or used in combination with other active ingredients such as fungicides, insecticidal and acaricidal agents, nematicides and soil pesticides; plant regulators, synergists, fertilizers, soil conditioners, animal feeds and the like.

A combination of the compound of the present invention and other active ingredients can be expected to have a synergistic effect on insecticidal, acaricidal and nematicidal activities. The synergistic effect can be confirmed by the Colby's formula (Colby, S. R.; Calculating Synergistic and Antagonistic Responses of Herbicide Combinations; Weeds 15, pp. 20-22, 1967) according to a conventional method.

Specific examples of insecticidal/acaricidal agents, nematicides, soil pesticides, anthelmintics and the like which can be mixed with or used in combination with the pest control agent of the present invention are shown below.

(1) Acetylcholinesterase inhibitors:

(a) carbamate-based inhibitors: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylylcarb, fenothiocarb, MIPC, MPMC, MTMC, aldoxycarb, allyxycarb, aminocarb, bufencarb, cloethocarb, metam sodium, promecarb;

(b) Organophosphorus-based inhibitors: acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimphos, temephos, terbufos, tetrachlorvinphos, thiometon, triazophos, trichlorfon, vamidothion; bromophos-ethyl, BRP, carbophenothion, cyanofenphos, demeton-S-methyl sulfone, dialifos, dichlofenthion, dioxabenzofos, etrimfos, fensulfothion, flupyrazofos, fonofos, formothion, fosmethilan, isazofos, iodofenphos, methacrifos, pirimiphos-ethyl, phosphocarb, propaphos, prothoate, sulprofos.

(2) GABA-gated chloride channel antagonists: acetoprole, chlordane, endosulfan, ethiprole, fipronil, pyrafluprole, pyriprole; camphechlor, heptachlor, dienochlor.

(3) Sodium channel modulators: acrinathrin, d-cis/trans allethrin, d-trans-allethrin, bifenthrin, bioallethrin, bioallethrin S-cyclopentyl isomers, bioresmethrin, cycloprothrin, cyfluthrin, beta-cyfluthrin, cyhalothrin, lambda-cyhalothrin, ganma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R)-isomers], esfenvalerate, etofenprox, fenpropathrin, fenvalerate, flucythrinate, flumethrin, taufluvalinate, halfenprox, imiprothrin, kadethrin, permethrin, phenothrin [(1R)-trans isomers], prallethrin, pyrethrum, resmethrin, silafluofen, tefluthrin, tetramethrin [(1R)-isomers], tralomethrin, transfluthrin, allethrin, pyrethrin, pyrethrin I, pyrethrin II, profluthrin, dimefluthrin, bioethanomethrin, biopermethrin, transpermethrin, fenfluthrin, fenpirithrin, flubrocythrinate, flufenprox, metofluthrin, protrifenbute, pyresmethrin, terallethrin.

(4) Nicotinic acetylcholine receptor agonists: acetamiprid, clothianidin, dinotefuran, imidacloprid, nitenpyram, nithiazine, thiacloprid, thiamethoxam, sulfoxaflor, nicotine, flupyradifurone, flupyrimin.

(5) Nicotinic acetylcholine receptor allosteric modulators: spinetoram, spinosad.

(6) Chloride channel activators: abamectin, emamectin benzoate, lepimectin, milbemectin; ivermectin, selamectin, doramectin, eprinomectin, moxidectin, milbemycin, milbemycin oxime, nemadectin.

(7) Juvenile hormone analogues: hydroprene, kinoprene, methoprene, fenoxycarb, pyriproxyfen, diofenolan, epofenonane, triprene.

(8) Other nonspecific inhibitors: methyl bromide, chloropicrin, sulfuryl fluoride, borax, tartar emetic.

(9) Homoptera selective antifeedants: flonicamid, pymetrozine, pyrifluquinazon.

(10) Mite growth inhibitors: clofentezine, diflovidazin, hexythiazox, etoxazole.

(11) Insect midgut inner membrane distrupting agents derived from microorganisms: *Bacillus thuringiensis* subsp. *israelensi*, *Bacillus sphaericus*, *Bacillus thuringiensis* subsp. *aizawai*, *Bacillus thuringiensis* subsp. *kurstaki*, *Bacillus thuringiensis* subsp. *tenebrionis*, Bt crop proteins, Cry1Ab, Cry1Ac, Cry1Fa, Cry1A.105, Cry2Ab, Vip3A, mCry3A, Cry3Ab, Cry3Bb, Cry34Ab1/Cry35Ab1.

(12) Mitochondrial ATP biosynthetic enzyme inhibitors: diafenthiuron, azocyclotin, cyhexatin, fenbutatin oxide, propargite, tetradifon.

(13) Oxidative phosphorylation uncouplers: chlorfenapyr, sulfluramid, DNOC; binapacryl, dinobuton, dinocap.

(14) Nicotinic acetylcholine receptor channel blockers: bensultap, cartap hydrochloride, nereistoxin, thiosultap-sodium salt, thiocyclam.

(15) Chitin synthesis inhibitors: bistrifluron, chlorfluazuron, diflubenzuron, flucycloxuron, flufenoxuron, hexaflumuron, lufenuron, novaluron, noviflumuron, teflubenzuron, triflumuron, buprofezin, fluazuron.

(16) Diptera molting disrupting agents: cyromazine.

(17) Molting hormone receptor agonists: chromafenozide, halofenozide, methoxyfenozide, tebufenozide.

(18) Octopamine receptor agonists: amitraz, demiditraz, chlordimeform.

(19) Mitochondrial electron transport system complex III inhibitors: acequinocyl, fluacrypyrim, hydramethylnon, bifenazate.

(20) Mitochondrial electron transport system complex I inhibitors: fenazaquin, fenpyroximate, pyrimidifen, pyridaben, tebufenpyrad, tolfenpyrad, rotenone.

(21) Voltage-dependent sodium channel blockers: indoxacarb, metaflumizone.

(22) Acetyl CoA carboxylase inhibitors: spirodiclofen, spiromesifen, spirotetramat, spiropidion.

(23) Mitochondrial electron transport system complex IV inhibitors: aluminum phosphide, calcium phosphide, phosphine, zinc phosphide, cyanide.

(24) Mitochondrial electron transport system complex II inhibitors: cyenopyrafen, cyflumetofen, pyflubumide.

(25) Ryanodine receptor modulators: chlorantraniliprole, cyantraniliprole, flubendiamide, cyclaniliprole, tetraniliprole.

(26) Mixed function oxidase inhibitor compounds: piperonyl butoxide.

(27) Latrophilin receptor agonists: depsipeptide, cyclic depsipeptide, 24-membered cyclic depsipeptide, emodepside.

(28) Other agents (with unknown action mechanisms): acynonapyr, azadirachtin, benzoximate, bromopropylate, chinomethionate, cryolite, dicofol, pyridalyl, benclothiaz, sulfur, amidoflumet, 1,3-dichloropropene, DCIP, phenisobromolate, benzomate, metaldehyde, chlorobenzilate, clothiazoben, dicyclanil, fenoxacrim, fentrifanil, flubenzimine, fluphenazine, gossyplure, japonilure, metoxadiazone, petroleum, sodium oleate, tetrasul, triarathene, afidopyropen, flometoquin, flufiprole, fluensulfone, meperfluthrin, tetramethylfluthrin, tralopyril, methylneodecanamide, fluralaner, afoxolaner, fluxametamide, 5-[5-(3,5-dichlorophenyl)-5-trifluoromethyl-4,5-dihydroisoxazol-3-yl]-2-(1H-1,2,4-triazol-1-yl) benzonitrile (CAS: 943137-49-3), broflanilide, triflumezopyrim, dicloromezotiaz, oxazosulfyl, other metadiamides, tyclopyrazoflor.

(29) Anthelmintics:
(a) benzimidazole-based anthelmintics: fenbendazole, albendazole, triclabendazole, oxibendazole, mebendazole, oxfendazole, parbendazole, flubendazole; febantel, netobimin, thiophanate; thiabendazole, cambendazole;
(b) salicylanilide-based anthelmintics: closantel, oxyclozanide, rafoxanide, niclosamide;
(c) substituted phenol-based anthelmintics: nitroxinil, nitroscanate;
(d) pyrimidine-based anthelmintics: pyrantel, morantel;
(e) imidazothiazole-based anthelmintics: levamisole, tetramisole;
(f) tetrahydropyrimidine-based anthelmintics: praziquantel, epsiprantel; and
(g) other anthelmintics: cyclodien, ryania, clorsulon, metronidazole, demiditraz; piperazine, diethylcarbamazine, dichlorophen, monepantel, tribendimidine, amidantel; thiacetarsamide, melorsamine, arsenamide.

Specific examples of the fungicide which can be mixed with or used in combination with the pest control agent of the present invention are shown below.

(1) Nucleic Acid Biosynthesis Inhibitors:
(a) RNA polymerase I inhibitors: benalaxyl, benalaxyl-M, furalaxyl, metalaxyl, metalaxyl-M; oxadixyl; clozylacon, ofurace;
(b) adenosine deaminase inhibitors: bupirimate, dimethirimol, ethirimol;
(c) DNA/RNA synthesis inhibitors: hymexazol, octhilinone;
(d) DNA topoisomerase II inhibitors: oxolinic acid.

(2) Mitotic Inhibitors and Cell Division Inhibitors:
- (a) β-tubulin polymerization inhibitors: benomyl, carbendazim, chlorfenazole, fuberidazole, thiabendazole, thiophanate, thiophanate methyl, diethofencarb, zoxamide, ethaboxam;
- (b) cell division inhibitors: pencycuron;
- (c) delocalization inhibitors of spectrin-like protein: fluopicolide.

(3) Respiratory Inhibitors:
- (a) complex I NADH oxidoreductase inhibitors: diflumetorim, tolfenpyrad;
- (b) complex II succinate dehydrogenase inhibitors: benodanil, flutolanil, mepronil, isofetamid, fluopyram, fenfuram, furmecyclox, carboxin, oxycarboxin, thifluzamide, benzovindiflupyr, bixafen, fluxapyroxad, furametpyr, isopyrazam, penflufen, penthiopyrad, sedaxane, boscalid, pyrapropoyne;
- (c) complex III ubiquinol oxidase Qo inhibitors: azoxystrobin, coumoxystrobin, coumethoxystrobin, enoxastrobin, flufenoxystrobin, picoxystrobin, pyraoxystrobin, pyraclostrobin, pyrametostrobin, triclopyricarb, kresoxim-methyl, trifloxystrobin, dimoxystrobin, fenaminstrobin, metominostrobin, orysastrobin, famoxadone, fluoxastrobin, fenamidone, pyribencarb;
- (d) complex III ubiquinol reductase Qi inhibitors: cyazofamid, amisulbrom;
- (e) oxidative phosphorylation uncouplers: binapacryl, meptyldinocap, dinocap, fluazinam, ferimzone;
- (f) oxidative phosphorylation inhibitors (ATP synthase inhibitors): fentin acetate, fentin chloride, fentin hydroxide;
- (g) ATP production inhibitor: silthiofam;
- (h) complex III: Qx (unknown) inhibitor of cytochrome bc1 (ubiquinone reductase): ametoctradin.

(4) Amino Acid and Protein Synthesis Inhibitors
- (a) methionine biosynthesis inhibitors: andoprim, cyprodinil, mepanipyrim, pyrimethanil;
- (b) protein synthesis inhibitors: blasticidin S, kasugamycin, kasugamycin hydrochloride, streptomycin, oxytetracycline.

(5) Signal Transduction Inhibitors:
- (a) Signal transduction inhibitors: quinoxyfen, proquinazid;
- (b) MAP/histidine kinase inhibitors in osmotic signal transduction: fenpiclonil, fludioxonil, chlozolinate, iprodione, procymidone, vinclozolin.

(6) Lipid and Cell Membrane Synthesis Inhibitors:
- (a) phospholipid biosynthesis and methyltransferase inhibitors: edifenphos, iprobenfos, pyrazophos, isoprothiolane;
- (b) lipid peroxidation agents: biphenyl, chloroneb, dicloran, quintozene, teenazene, tolclofos-methyl, etridiazole;
- (c) agents acting on cell membranes: iodocarb, propamocarb, propamocarb hydrochloride, propamocarb-fosetylate, prothiocarb;
- (d) microorganisms disturbing pathogenic cell membranes: *Bacillus subtilis, Bacillus subtilis* strain QST713, *Bacillus subtilis* strain FZB24, *Bacillus subtilis* strain MBI600, *Bacillus subtilis* strain D747;
- (e) agents disturbing cell membranes: extracts of *Melaleuca alternifolia* (tea tree).

(7) Sterol Biosynthesis Inhibitors of Cell Membranes:
- (a) C14 demethylation inhibitors in sterol biosynthesis: triforine, pyrifenox, pyrisoxazole, fenarimol, flurprimidol, nuarimol; imazalil, imazalil sulfate, oxpoconazole, pefurazoate, prochloraz, triflumizole, viniconazole, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, fluconazole, furconazole-cis, hexaconazole, imibenconazole, ipconazole, metconazole, myclobutanil, penconazole, propiconazole, fluquinconazole, simeconazole, tebuconazole, tetraconazole, triadimefon, triadimenol, triticonazole, prothioconazole, voriconazole;
- (b) inhibitors of Δ14 reductase and Δ8→Δ7-isomerase in sterol biosynthesis: aldimorph, dodemorph, dodemorph acetate, fenpropimorph, tridemorph, fenpropidine, piperalin, spiroxamine;
- (c) 3-keto reductase inhibitors in C4 demethylation in sterol biosynthesis system: fenhexamid, fenpyrazamine;
- (d) squalene epoxidase inhibitors in sterol biosynthesis system: pyributicarb; naftifine, terbinafine.

(8) Cell wall synthesis inhibitors
- (a) trehalase inhibitor: validamycin;
- (b) chitin synthase inhibitors: polyoxins, polyoxorim;
- (c) cellulose synthase inhibitors: dimethomorph, flumorph, pyrimorph, benthiavalicarb, iprovalicarb, tolprocarb, valifenalate, mandipropamid.

(9) Melanin biosynthesis inhibitors
- (a) reductase inhibitors in melanin biosynthesis: fthalide, pyroquilon, tricyclazole;
- (b) anhydrase inhibitors in melanin biosynthesis: carpropamid, diclocymet, fenoxanil;

(10) Resistance inducers of host plants:
- (a) agent acting on salicylic acid synthetic pathway: acibenzolar-S-methyl;
- (b) other agents: probenazole; tiadinil; isotianil; laminarin; *Reynoutria sachalinensis* extract.

(11) agents with unknown actions: cymoxanil, fosetyl-aluminium, phosphoric acid (phosphates), tecloftalam, triazoxide, flusulfamide, diclomezine, methasulfocarb, cyflufenamid, metrafenone, pyriofenone, dodine, dodine free base, flutianil.

(12) agents having multiple points of action: copper (copper salts), Bordeaux mixture, copper hydroxide, copper naphthalate, copper oxide, copper oxychloride, copper sulfate, sulfur, sulfur products, calcium polysulfide; ferbam, mancozeb, maneb, mancopper, metiram, polycarbamate, propineb, thiram, zineb, ziram, captan, captafol, folpet, chlorothalonil, dichlofluanid, tolylfluanid, guazatine, iminoctadine acetates (iminoctadine triacetate), iminoctadine albesilates (iminoctadine trialbesilate), anilazine, dithianon, chinomethionate, fluoroimide.

(13) Other agents: DBEDC, fluorofolpet, guazatine acetate, bis(8-quinolinolato)copper(II), propamidine, chloropicrin, cyprofuram, agrobacterium, bethoxazin, diphenylamine, methyl isothiocyanate (MITC), mildiomycin, capsaicin, cufraneb, cyprosulfamide, dazomet, debacarb, dichlorophen, difenzoquat, difenzoquat methyl sulfate, flumetover, fosetyl calcium, fosetyl sodium, irumamycin, natamycin, nitrothal-isopropyl, oxamocarb, propanosine-sodium, pyrrolnitrin, tebufloquin, tolnifanide, zarilamid, algophase, amicarthiazol, oxathiapiprolin, metiram zinc, benthiazole, trichlamide, uniconazole, mildiomycin, oxyfenthiin, picarbutrazox.

Specific examples of plant regulators which can be mixed with or used in combination with the pest control agent of the present invention are shown below. 1-Methylcyclopropene, 2,3,5-triiodobenzoic acid, IAA, IBA, MCPA, MCPB, 4-CPA, 5-aminolevulinic acid hydrochloride, 6-benzylaminopurine, abscisic acid, aviglycine hydrochloride, ancymidol, butralin, calcium carbonate, calcium chloride, calcium formate, calcium peroxide, lime sulfur, calcium sulfate, chlormequat chloride, chlorpropham, choline chloride, cloprop, cyanamide, cyclanilide, daminozide, decyl alcohol, dichlorprop, dikegulac, dimethipin, diquat, ethephon, ethychlozate, flumetralin, flurprimidol, forchlorfenuron, gibberellin A, gibberellin A3, hymexazol, inabenfide, isoprothiolane, kinetin, maleic hydrazide, mefluidide, mepiquat chloride, oxidized glutathione, paclobutrazol, pendimethalin, prohexadione calcium, prohydrojasmon, pyraflufenethyl, sintofen, sodium 1-naphthaleneacetate, sodium cyanate, streptomycin, thidiazuron, triapenthenol, tribufos, trinexapac-ethyl, uniconazole P, and 1-naphthylacetamide.

[Ectoparasite Control Agent]

The ectoparasite control agent of the present invention contains at least one selected from the pyridinium salts of the present invention as an active ingredient. The amount of the compound of the present invention contained in the ectoparasite control agent of the present invention is not particularly limited as long as it shows the effect of controlling ectoparasites, but it is usually preferably within the range of 0.01 to 95 parts by mass with respect to 100 parts by mass of the control agent of the present invention.

Examples of host animals to be treated with the ectoparasite control agent of the present invention include warm-blooded animals including pet animals such as dogs and cats; pet birds; domestic animals such as cattle, horses, pigs and sheep; domestic fowls; and the like. In addition, honey bees, stag beetles and beetles can be exemplified.

The ectoparasite control agent of the present invention can be applied by a known veterinary method (topical, oral, parenteral or subcutaneous administration). As a method therefor, a method of orally administering tablets, capsules, mixed feeds or the like to the animals; a method of administering to the animals by using an immersion liquid, suppository, injection (intramuscular, subcutaneous, intravenous, intraperitoneal or the like) or the like; a method of topically administering by spraying, pouring-on or spotting-on an oily or aqueous liquid preparation; a method of kneading an ectoparasite control agent in a resin, molding the kneaded product into an appropriate shape such as a collar, ear tag or the like, and attaching and topically administering the resultant to the animals; and the like can be mentioned.

Ectoparasites are parasitic in and on host animals, especially warm-blooded animals. More specifically, the ectoparasites are parasitic in and on the back, armpit, lower abdomen, inner thigh and the like of the host animals and obtain nutritional sources such as blood and dandruff from the animals to live. Examples of ectoparasites include mites and ticks, lice, fleas, mosquitoes, stable flies, flesh flies and the like. Specific examples of the ectoparasites which can be controlled by the ectoparasite control agent of the present invention are shown below.

(1) Acari

Mites and ticks belonging to the family Dermanyssidae, mites and ticks belonging to the family Macronyssidae, mites and ticks belonging to the family Laelapidae, mites and ticks belonging to the family Varroidae, mites and ticks belonging to the family Argasidae, mites and ticks belonging to the family Ixodidae, mites and ticks belonging to the family Psoroptidae, mites and ticks belonging to the family Sarcoptidae, mites and ticks belonging to the family Knemidokoptidae, mites and ticks belonging to the family Demodixidae, mites and ticks belonging to the family Trombiculidae, insect-parasitic mites and ticks such as *Coleopterophagus berlesei* or the like.

(2) Phthiraptera

Lice belonging to the family Haematopinidae, lice belonging to the family Linognathidae, biting lice belonging to the family Menoponidae, biting lice belonging to the family Philopteridae, biting lice belonging to the family Trichodectidae.

(3) Siphonaptera

Fleas of the family Pulicidae, for example, species belonging to the genus *Ctenocephalides* (*Ctenocephalides* spp.) such as *Ctenocephalides canis* and *Ctenocephalides felis*;

fleas belonging to the family Tungidae, fleas belonging to the family Ceratophyllidae, fleas belonging to the family Leptopsyllidae.

(4) Hemiptera (5) Insect Pests of the Order Diptera

Mosquitoes belonging to the family Culicidae, black flies belonging to the family Simuliidae, biting midges belonging to the family Ceratopogonidae, horseflies belonging to the family Tabanidae, flies belonging to the family Muscidae, tsetse flies belonging to the family Glossinidae; flesh flies belonging to the family Sarcophagidae, flies belonging to the family Hippoboscidae, flies belonging to the family Calliphoridae, flies belonging to the family Oestridae.

[Endoparasite Control- or Exterminating Agent]

The endoparasite control- or exterminating agent of the present invention contains at least one selected from the pyridinium salts of the present invention as an active ingredient. The amount of the compound of the present invention contained in the endoparasite control- or exterminating agent of the present invention is not particularly limited as long as it shows the effect of controlling endoparasites, but it is usually preferably within the range of 0.01 to 95 parts by mass with respect to 100 parts by mass of the control- or exterminating agent of the present invention.

The parasite to be targeted by the endoparasite control- or exterminating agent of the present invention is parasitic (endoparasitic) in host animals, especially warm blooded animals and fish. Examples of host animals for which the endoparasite control- or exterminating agent of the present invention is effective include warm-blooded animals such as humans, domestic mammals (for example, cattle, horses, pigs, sheep, goats and the like), laboratory animals (for example, mice, rats, gerbils and the like), pet animals (for example, hamsters, guinea pigs, dogs, cats, horses, squirrels, rabbits, ferrets, and the like), wild and zoo mammals (monkeys, foxes, deers, buffaloes and the like), domestic fowls (turkeys, ducks, chickens, quails, geese and the like) and pet birds (pigeons, parrots, hill mynas, Java sparrows, parakeets, society finches, canaries and the like); or fish such as salmon, trout and nishikigoi. By controlling and exterminating parasites, it is possible to prevent or treat parasitic diseases mediated by the parasites.

Examples of the parasites to be controlled or exterminated include the followings.

(1) Nematodes of the Order Dioctophymatida (a) kidney worms of the family Dioctophymatidae, for example, species belonging to the genus *Dioctophyma* (*Dioctophyma* spp.) such as *Dioctophyma renale*; and (b) kidney worms of the family Soboliphymatidae, for example, species belonging to the genus *Soboliphyme* (*Soboliphyme* spp.) such as *Soboliphyme abei* and *Soboliphyme baturini*.

(2) Nematodes of the Order Trichocephalida
  (a) trichina worms of the family Trichinellidae, for example, species belonging to the genus *Trichinella* (*Trichinella* spp.) such as *Trichinella spiralis*; and
  (b) whipworms of the family Trichuridae, for example, species belonging to the genus *Capillaria* (*Capillaria* spp.) such as *Capillaria annulata, Capillaria contorta, Capillaria hepatica, Capillaria perforans, Capillaria plica,* and *Capillaria suis*; and species belonging to the genus *Trichuris* (*Trichuris* spp.) such as *Trichuris vulpis, Trichuris discolor, Trichuris ovis, Trichuris skrjabini,* and *Trichuris suis.*

(3) Nematodes of the Order Rhabditida
  threadworms of the family Strongyloididae, for example, species belonging to the genus *Strongyloides* (*Strongyloides* spp.) such as *Strongyloides papillosus, Strongyloides planiceps, Strongyloides ransomi, Strongyloides suis, Strongyloides stercoralis, Strongyloides tumefaciens,* and *Strongyloides ratti.*

(4) Nematodes of the Order Strongylida
  hookworms of the family Ancylostomatidae, for example, species belonging to the genus *Ancylostoma* (*Ancylostoma* spp.) such as *Ancylostoma braziliense, Ancylostoma caninum, Ancylostoma duodenale,* and *Ancylostoma tubaeforme*; species belonging to the genus *Uncinaria* (*Uncinaria* spp.) such as *Uncinaria stenocephala*; and species belonging to the genus *Bunostomum* (*Bunostomum* spp.) such as *Bunostomum phlebotomum* and *Bunostomum trigonocephalum.*

(5) Nematodes of the Order Strongylida
  (a) nematodes of the family Angiostrongylidae, for example, species belonging to the genus *Aelurostrongylus* (*Aelurostrongylus* spp.) such as *Aelurostrongylus abstrusus*; and species belonging to the genus *Angiostrongylus* (*Angiostrongylus* spp.) such as *Angiostrongylus vasorum* and *Angiostrongylus cantonesis*;
  (b) nematodes of the family Crenosomatidae, for example, species belonging to the genus *Crenosoma* (*Crenosoma* spp.) such as *Crenosoma aerophila* and *Crenosoma vulpis*;
  (c) nematodes of the family Filaroididae, for example, species belonging to the genus *Filaroides* (*Filaroides* spp.) such as *Filaroides hirthi* and *Filaroides osleri*;
  (d) lungworms of the family Metastrongylidae, for example, species belonging to the genus *Metastrongylus* (*Metastrongylus* spp.) such as *Metastrongylus apri, Metastrongylus asymmetricus, Metastrongylus pudendotectus* and *Metastrongylus salmi*; and
  (e) gapeworms of the family Syngamidae, for example, species belonging to the genus *Cyathostoma* (*Cyathostoma* spp.) such as *Cyathostoma bronchialis*; and species belonging to the genus *Syngamus* (*Syngamus* spp.) such as *Syngamus skrjabinomorpha* and *Syngamus trachea.*

(6) Nematodes of the Order Strongylida
  (a) nematodes of the family Molineidae, for example, species belonging to the genus *Nematodirus* (*Nematodirus* spp.) such as *Nematodirus filicollis* and *Nematodirus spathiger*;
  (b) nematodes of the family Dictyocaulidae, for example, species belonging to the genus *Dictyocaulus* (*Dictyocaulus* spp.) such as *Dictyocaulus filaria* and *Dictyocaulus viviparus*;
  (c) nematodes of the family Haemonchidae, for example, species belonging to the genus *Haemonchus* (*Haemonchus* spp.) such as *Haemonchus contortus*; and species belonging to the genus *Mecistocirrus* (*Mecistocirrus* spp.) such as *Mecistocirrus digitatus*;
  (d) nematodes of the family Haemonchidae, for example, species belonging to the genus *Ostertagia* (*Ostertagia* spp.) such as *Ostertagia ostertagi*;
  (e) nematodes of the family Heligmonellidae, for example, species belonging to the genus *Nippostrongylus* (*Nippostrongylus* spp.) such as *Nippostrongylus braziliensis*; and
  (f) nematodes of the family Trichostrongylidae, for example, species belonging to the genus *Trichostrongylus* (*Trichostrongylus* spp.) such as *Trichostrongylus axei, Trichostrongylus colubriformis* and *Trichostrongylus tenuis*; species belonging to the genus *Hyostrongylus* (*Hyostrongylus* spp.) such as *Hyostrongylus rubidus*; and species belonging to the genus *Obeliscoides* (*Obeliscoides* spp.) such as *Obeliscoides cuniculi.*

(7) Nematodes of the Order Strongylida
  (a) nematodes of the family Chabertiidae, for example, species belonging to the genus *Chabertia* (*Chabertia* spp.) such as *Chabertia ovina*; and species belonging to the genus *Oesophagostomum* (*Oesophagostomum* spp.) such as *Oesophagostomum brevicaudatum, Oesophagostomum columbianum, Oesophagostomum dentatum, Oesophagostomum georgianum, Oesophagostomum maplestonei, Oesophagostomum quadrispinulatum, Oesophagostomum radiatum, Oesophagostomum venulosum* and *Oesophagostomum watanabei*;
  (b) nematodes of the family Stephanuridae, for example, species belonging to the genus *Stephanurus* (*Stephanurus* spp.) such as *Stephanurus dentatus*; and
  (c) nematodes of the family Strongylidae, for example, species belonging to the genus *Strongylus* (*Strongylus* spp.) such as *Strongylus asini, Strongylus edentatus, Strongylus equinus* and *Strongylus vulgaris.*

(8) Nematodes of the Order Oxyurida
  nematodes of the family Oxyuridae, for example, species belonging to the genus *Enterobius* (*Enterobius* spp.) such as *Enterobius anthropopitheci* and *Enterobius vermicularis*; species belonging to the genus *Oxyuris* (*Oxyuris* spp.) such as *Oxyuris equi*; and species belonging to the genus *Passalurus* (*Passalurus* spp.) such as *Passalurus ambiguus.*

(9) Nematodes of the Order Ascaridida
  (a) nematodes of the family Ascaridiidae, for example, species belonging to the genus *Ascaridia* (*Ascaridia* spp.) such as *Ascaridia galli*;
  (b) nematodes of the family Heterakidae, for example, species belonging to the genus *Heterakis* (*Heterakis* spp.) such as *Heterakis beramporia, Heterakis brevispiculum, Heterakis gallinarum, Heterakis pusilla* and *Heterakis putaustralis*;
  (c) nematodes of the family Anisakidae, for example, species belonging to the genus *Anisakis* (*Anisakis* spp.) such as *Anisakis simplex*;
  (d) nematodes of the family Ascarididae, for example, species belonging to the genus *Ascaris* (*Ascaris* spp.) such as *Ascaris lumbricoides* and *Ascaris suum*; and species belonging to the genus *Parascaris* (*Parascaris* spp.) such as *Parascaris equorum*; and
  (e) nematodes of the family Toxocaridae, for example, species belonging to the genus *Toxocara* (*Toxocara* spp.) such as *Toxocara canis, Toxocara leonina, Toxocara suum, Toxocara vitulorum* and *Toxocara cati.*

(10) Nematodes of the Order Spirurida
  (a) nematodes of the family Onchocercidae, for example, species belonging to the genus *Brugia* (*Brugia* spp.) such as *Brugia malayi, Brugia pahangi* and *Brugia patei*; species belonging to the genus *Dipetalonema* (*Dipetalonema* spp.) such as *Dipetalonema reconditum*; species belonging to the genus *Dirofilaria* (*Dirofilaria* spp.) such as *Dirofilaria immitis*; species belonging to the genus *Filaria* (*Filaria* spp.) such as *Filaria oculi*; and species belonging to the genus *Onchocerca* (*Onchocerca* spp.) such as *Onchocerca cervicalis*, *Onchocerca gibsoni* and *Onchocerca gutturosa*;

(b) nematodes of the family Setariidae, for example, species belonging to the genus *Setaria* (*Setaria* spp.) such as *Setaria digitata*, *Setaria equina*, *Setaria labiatopapillosa* and *Setaria marshalli*; and species belonging to the genus *Wuchereria* (*Wuchereria* spp.) such as *Wuchereria bancrofti*; and (c) nematodes of the family Filariidae, for example, species belonging to the genus *Parafilaria* (*Parafilaria* spp.) such as *Parafilaria multipapillosa*; and species belonging to the genus *Stephanofilaria* (*Stephanofilaria* spp.) such as *Stephanofilaria assamensis*, *Stephanofilaria dedoesi*, *Stephanofilaria kaeli*, *Stephanofilaria okinawaensis* and *Stephanofilaria stilesi*.

(11) Nematodes of the Order Spirurida (a) nematodes of the family Gnathostomatidae, for example, species belonging to the genus *Gnathostoma* (*Gnathostoma* spp.) such as *Gnathostoma doloresi* and *Gnathostoma spinigerum*;

(b) nematodes of the family Habronematidae, for example, species belonging to the genus *Habronema* (*Habronema* spp.) such as *Habronema majus*, *Habronema microstoma* and *Habronema muscae*; and species belonging to the genus *Draschia* (*Draschia* spp.) such as *Draschia megastoma*;

(c) nematodes of the family Physalopteridae, for example, species belonging to the genus *Physaloptera* (*Physaloptera* spp.) such as *Physaloptera canis*, *Physaloptera cesticillata*, *Physaloptera erdocyona*, *Physaloptera felidis*, *Physaloptera gemina*, *Physaloptera papilloradiata*, *Physaloptera praeputialis*, *Physaloptera pseudopraerutialis*, *Physaloptera rara*, *Physaloptera sibirica* and *Physaloptera vulpineus*;

(d) nematodes of the family Gongylonematidae, for example, species belonging to the genus *Gongylonema* (*Gongylonema* spp.) such as *Gongylonema pulchrum*;

(e) nematodes of the family Spirocercidae, for example, species belonging to the genus *Ascarops* (*Ascarops* spp.) such as *Ascarops strongylina*; and (f) nematodes of the family Thelaziidae, for example, species belonging to the genus *Thelazia* (*Thelazia* spp.) such as *Thelazia callipaeda*, *Thelazia gulosa*, *Thelazia lacrymalis*, *Thelazia rhodesi* and *Thelazia skrjabini*.

[Control Agents for Other Pests]

In addition, the compound of the present invention is excellent in the effect of controlling insect pests having a stinger or venom which harm humans and animals, insect pests that mediate various pathogens/pathogenic microbes, and insect pests that cause discomfort to humans (such as toxic pests, hygiene pests and unpleasant pests).

Specific examples thereof are shown below.

(1) Insect Pests of the Order Hymenoptera

Bees belonging to the family Argidae, bees belonging to the family Cynipidae, bees belonging to the family Diprionidae, ants belonging to the family Formicidae, bees belonging to the family Mutillidae, bees belonging to the family Vespidae.

(2) Other Pests

Cockroaches (Blattodea), termites, spiders (Araneae), centipedes, millipedes, crustaceans, bedbugs (*Cimex lectularius*).

EXAMPLES

[Pharmaceutical Formulation]

Although some pharmaceutical formulations of the pest control agent, insecticidal or acaricidal agent, ectoparasite control agent, or endoparasite control- or exterminating agent of the present invention are shown, additives and the addition ratios should not be limited to these examples and can be modified over a wide range. The term "part" in the formulations indicates "part by weight".

The formulations for agricultural and horticultural use and for paddy rice are shown below.

(Formulation 1: Wettable Powder)

40 parts of the compound of the present invention, 53 parts of diatomaceous earth, 4 parts of a higher alcohol sulfuric acid ester and 3 parts of an alkyl naphthalene sulfonate are uniformly mixed and finely pulverized to obtain a wettable powder containing 40% of an active ingredient.

(Formulation 2: Emulsion)

30 parts of the compound of the present invention, 33 parts of xylene, 30 parts of dimethylformamide and 7 parts of a polyoxyethylene alkyl allyl ether are mixed and dissolved to obtain an emulsion containing 30% of an active ingredient.

(Formulation 3: Granule)

5 parts of the compound of the present invention, 40 parts of talc, 38 parts of clay, 10 parts of bentonite and 7 parts of a sodium alkylsulfate are uniformly mixed and finely pulverized, and then granulated into a granular form having a diameter of 0.5 to 1.0 mm to obtain a granule containing 5% of an active ingredient.

(Formulation 4: Granule)

5 parts of the compound of the present invention, 73 parts of clay, 20 parts of bentonite, 1 part of sodium dioctyl sulfosuccinate and 1 part of potassium phosphate are thoroughly ground and mixed, water is added and thoroughly kneaded, followed by granulation and drying to obtain a granule containing 5% of an active ingredient.

(Formulation 5: Suspension)

10 parts of the compound of the present invention, 4 parts of a polyoxyethylene alkyl allyl ether, 2 parts of a polycarboxylic acid sodium salt, 10 parts of glycerin, 0.2 parts of xanthan gum and 73.8 parts of water are mixed and subjected to wet grinding until the particle size becomes 3 microns or less to obtain a suspension containing 10% of an active ingredient.

The formulations of an ectoparasite control agent or an endoparasite control- or exterminating agent are shown below.

(Formulation 6: Granule)

5 parts of the compound of the present invention are dissolved in an organic solvent to obtain a solution, the solution is sprayed onto 94 parts of kaolin and 1 part of white carbon, and then the solvent is evaporated under reduced pressure. This type of granule can be mixed with animal feed.

(Formulation 7: Injection)

0.1 to 1 part of the compound of the present invention and 99 to 99.9 parts of peanut oil are uniformly mixed and then sterilized by filtration through a sterilizing filter.

(Formulation 8: Pour-on Agent)

5 parts of the compound of the present invention, 10 parts of a myristic acid ester and 85 parts of isopropanol are uniformly mixed to obtain a pour-on agent.

(Formulation 9: Spot-on Agent)

10 to 15 parts of the compound of the present invention, 10 parts of a palmitic acid ester and 75 to 80 parts of isopropanol are uniformly mixed to obtain a spot-on agent.

(Formulation 10: Spraying Agent)

1 part of the compound of the present invention, 10 parts of propylene glycol and 89 parts of isopropanol are uniformly mixed to obtain a spraying agent.

Next, the present invention will be described in more detail by showing synthesis examples. However, the present invention is in no way limited by the following examples.

Example 1

(Z)-(2-chloro-3-(4-trifluoromethoxy)phenyl)acryloyl)(pyridin-1-ium-1-yl)amide

Synthesis of [(Z)-(2-chloro-3-(4-(trifluoromethoxy)phenyl)acryloyl)(pyridin-1-ium-1-yl)amide]

[Step 1]

Ethyl (Z)-2-chloro-3-(4-(trifluoromethoxy)phenyl)acrylate

Synthesis of [ethyl (Z)-2-chloro-3-(4-(trifluoromethoxy)phenyl) acrylate]

[Chemical Formula 21]

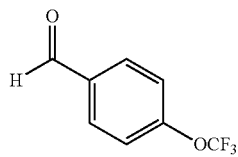

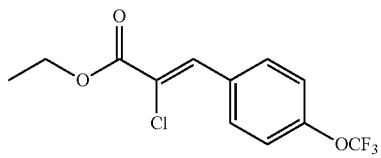

A Horner-Emmons reagent (3.1 g) was dissolved in THF (10 ml), 60% NaH was added thereto under ice cooling, and the resulting mixture was stirred at room temperature for 30 minutes. 4-(Trifluoromethoxy)benzaldehyde (1.9 g) was added thereto under ice cooling, and the resulting mixture was stirred at room temperature for 1 hour. A saturated aqueous solution of ammonium chloride was added thereto, and the resulting mixture was extracted with ethyl acetate and washed with saturated brine. Thereafter, the organic layer was dried over anhydrous magnesium sulfate, filtered, and then the resulting filtrate was concentrated under reduced pressure. The obtained concentrate was purified by silica gel chromatography to obtain 2.04 g of the title compound at a yield of 69%.

[Step 2]

(Z)-2-chloro-3-(4-(trifluoromethoxy)phenyl)acrylic acid

Synthesis of [(Z)-2-chloro-3-(4-(trifluoromethoxy)phenyl)acrylic acid]

[Chemical Formula 22]

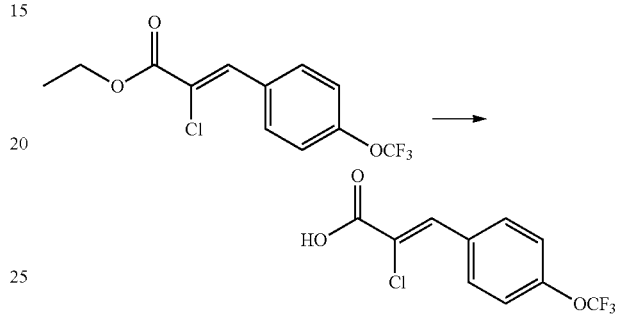

Ethyl (Z)-2-chloro-3-(4-(trifluoromethoxy)phenyl) acrylate (1.0 g) was dissolved in a mixed solvent of water (2 ml) and 10% KOH-EtOH (5 ml), and the resulting mixture was heated and stirred under reflux for 3 hours. The resultant was cooled to room temperature, and then the solvent was distilled off. Water and concentrated hydrochloric acid were added to the residue, and the resulting mixture was extracted with ethyl acetate. The organic layer was washed by adding saturated brine. Thereafter, the organic layer was dried over anhydrous magnesium sulfate, filtered, and then the solvent was distilled off to obtain 0.42 g of the title compound at a yield of 75%.

[Step 3]

(Z)-(2-chloro-3-(4-(trifluoromethoxy)phenyl)acryloyl) (pyridin-1-ium-1-yl)amide

Synthesis of [(Z)-(2-chloro-3-(4-(trifluoromethoxy)phenyl)acryloyl) (pyridin-1-ium-1-yl)amide]

[Chemical Formula 23]

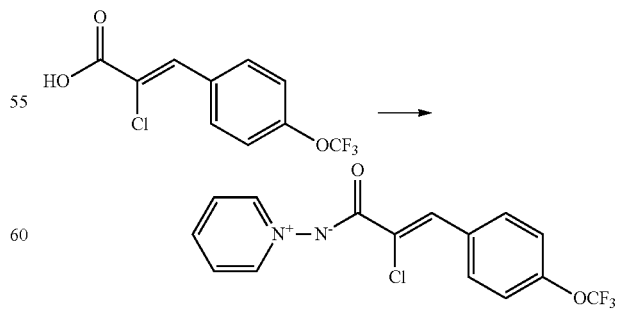

(Z)-2-chloro-3-(4-(trifluoromethoxy)phenyl)acrylic acid (0.64 g) was dissolved in chloroform (5 ml), oxalyl chloride (0.3 ml) and a catalytic amount of DMF were added thereto, and the resulting mixture was stirred at room temperature for 2 hours. The solvent was distilled off from the obtained liquid. Chloroform (5 ml), 1-aminopyridinium iodide (0.53 g) and triethylamine (3 ml) were added to the residue, and the resulting mixture was stirred at room temperature for 3 hours. The obtained liquid was concentrated under reduced pressure. A mixed solvent of ethyl acetate and hexane was added to the obtained concentrate, and the resulting mixture was recrystallized to obtain 0.54 g of the title compound at a yield of 66%.

Examples of the compounds of the present invention produced by the same method as in the above Examples are shown in Table 1. Table 1 shows the compounds represented by the formula (I-1) among the compounds of the present invention. In Table 1, Me represents a methyl group. A bond marked with a symbol * used for the notation of Y is bonded to a carbonyl group in a pyridinium salt, and a bond marked with a symbol ** is bonded to a phenyl group. Physical property data of the compounds were entered in the column of "Physical properties". As the physical property data, refractive indices (nD) or melting points (m.p.) were described.

NMR data for the compounds with compound numbers b-36, b-37, b-38, and b-42 are shown below.

b-36: $^1$H-NMR (CDCl$_3$, δ ppm) 2.22 (s, 3H), 4.46 (t, 2H), 6.82 (m, 1H), 6.98 (s, 1H), 7.11 (m, 1H), 7.29 (m, 1H), 7.62 (s, 1H), 7.67 (t, 2H), 7.92 (m, 1H), 8.74 (d, 2H).

b-37: $^1$H-NMR (CDCl$_3$, δ ppm) 2.23 (s, 3H), 7.52 (m, 2H), 7.56 (m, 2H), 7.67-7.71 (m, 1H), 7.95 (t, 1H), 8.75 (m, 2H).

b-38: $^1$H-NMR (CDCl$_3$, δ ppm) 2.21 (s, 3H), 7.17 (d, 2H), 7.41 (d, 2H), 7.63 (s, 1H), 7.68 (t, 2H), 7.93 (t, 1H), 8.73 (m, 2H).

b-42: $^1$H-NMR (CDCl$_3$, δ ppm) 2.25 (s, 3H), 7.56 (d, 2H), 7.67-7.69 (m, 3H), 7.87 (m, 2H), 7.94 (t, 1H), 8.74 (m, 2H), 10.00 (s, 1H).

(Chemical Formula 24)

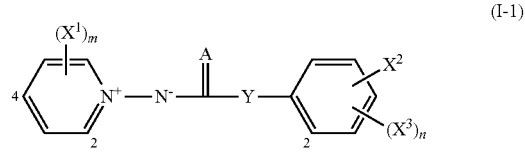

(I-1)

TABLE 1

| Compound Number | $(X^1)_m$ | A | Y | $X^2$ | $(X^3)_n$ | Physical Properties |
|---|---|---|---|---|---|---|
| b-1 | — | O | *─C(MeSO$_2$)=C(H)─** | 4-CF$_3$ | — | m.p. 177-180° C. |
| b-2 | — | O | *─C(MeS)=C(H)─** | 4-CF$_3$ | — | m.p. 117-119° C. |
| b-3 | — | O | *─C(Cl)=C(H)─** | 4-CF$_3$O | — | m.p. 128-130° C. |
| b-4 | — | O | *─C(C≡CH)=C(H)─** | 4-CF$_3$ | — | m.p. 144-147° C. |
| b-5 | — | O | *─C(Cl)=C(H)─** | 4-CF$_3$O | — | m.p. 147-149° C. |
| b-6 | — | O | *─C(Br)=C(H)─** | 4-CF$_3$ | — | m.p. 144-145° C. |

TABLE 1-continued

| Compound Number | $(X^1)_m$ | A | Y | $X^2$ | $(X^3)_n$ | Physical Properties |
|---|---|---|---|---|---|---|
| b-7 | — | O | *CH=CH** with Br on * carbon, H on ** | 4-CF$_3$ | — | m.p. 118-120° C. |
| b-8 | — | O | *CH=CH** with Cl on * carbon, H on ** | 4-CF$_3$ | — | m.p. 145-146° C. |
| b-9 | — | O | *CH=CH** with F on * carbon, H on ** | 4-CF$_3$ | — | m.p. 211-213° C. |
| b-10 | — | O | *CH=CH** with F on * carbon, H on ** | 4-CF$_3$ | — | m.p. 162-164° C. |
| b-11 | — | O | *C(OMe)=CH** with H on ** | 4-CF$_3$ | — | m.p. 125-127° C. |
| b-12 | — | O | *C(CH$_2$OMe)=CH** with H on ** | 4-CF$_3$ | — | m.p. 120-122° C. |
| b-13 | — | O | *C(Me)=CH** with H on ** | 4-CF$_3$O | — | m.p. 101-102° C. |
| b-14 | — | O | *CH=CH** with H,H | 4-CF$_3$ | — | m.p. 140-142° C. |
| b-15 | — | O | *CH=CH** with H,H | 2-MeO | — | nD(22.1)1.6263 |
| b-16 | — | O | *CH=CH** with H,H | 2-MeO | — | m.p. 155-156° C. |

TABLE 1-continued

| Compound Number | $(X^1)_m$ | A | Y | $X^2$ | $(X^3)_n$ | Physical Properties |
|---|---|---|---|---|---|---|
| b-17 | — | O | CH2=C(*)-CH(**)-Me (with H on **) | 4-CF$_3$ | — | m.p. 98-100° C. |
| b-18 | — | O | *-C(H)=C(**)-Me | 4-CF$_3$ | — | m.p. 114-114.5° C. |
| b-19 | — | O | *-C(Me)=C(**)-H | 4-CF$_3$ | — | m.p. 88-90° C. |
| b-20 | — | O | *-C(H)=C(**)-H with Me | 4-CF$_3$O | — | m.p. 105-107° C. |
| b-21 | — | O | *-C(H)=C(**)-Me | 4-CF$_3$ | — | m.p. 149-150° C. |
| b-22 | 4-CF$_3$ | O | *-CH=CH-** | 4-CF$_3$ | — | m.p. 247-250° C. |
| b-23 | — | O | *-CH=CH-CH=CH-** | 4-CF$_3$ | — | m.p. 177-178° C. |
| b-24 | 3-CO$_2$Me | O | *-CH=CH-** | 4-CF$_3$ | — | m.p. 212-214° C. |
| b-25 | 3-CF$_3$ | O | *-CH=CH-** | 4-CF$_3$ | — | m.p. 175-178° C. |
| b-26 | 3-Cl | O | *-CH=CH-** | 4-CF$_3$ | — | m.p. 169-171° C. |

TABLE 1-continued

| Compound Number | $(X^1)_m$ | A | Y | $X^2$ | $(X^3)_n$ | Physical Properties |
|---|---|---|---|---|---|---|
| b-27 | — | O | CH=CH (H,H) | 4-MeO | — | m.p. 143-144° C. |
| b-28 | — | O | CH=CH (H,H) | 4-$CF_3$O | — | m.p. 130-131° C. |
| b-29 | — | O | CH=CH (H,H) | 4-MeS | — | m.p. 167-169° C. |
| b-30 | — | O | CH=CH (H,H) | 4-$CF_3$ | — | m.p. 171-173° C. |
| b-31 | — | O | CH=CH (H,H) | 3-$CF_3$ | — | m.p. 116-118° C. |
| b-32 | — | O | CH=CH (H,H) | 4-$CF_3OCFHCF_2O$ | — | m.p. 150-152° C. |
| b-33 | — | O | CH=CH (H,H) | 4-$CF_3CFHCF_2O$ | — | m.p. 142-144° C. |
| b-34 | — | O | C(Me)=CH (H) | 4-$CF_3CF_2CF_2CF_2CH$=CH | — | m.p. 88-91° C. |
| b-35 | — | O | C(Me)=CH (H) | 4-$CF_3CF_2CH$=CH | — | m.p. 65-67° C. |
| b-36 | — | O | C(Me)=CH (H) | 3-$CF_3CF_2CF_2CH_2O$ | — | — |
| b-37 | — | O | C(Me)=CH (H) | 4-$CF_3CF_2CF_2CF_2$ | — | — |

TABLE 1-continued

| Compound Number | $(X^1)_m$ | A | Y | $X^2$ | $(X^3)_n$ | Physical Properties |
|---|---|---|---|---|---|---|
| b-38 | — | O | *-C(Me)=CH-** | 4-$CF_3CF_2CF_2OCFHCF_2O$ | — | — |
| b-39 | — | O | *-C(Me)=CH-** | 4-($CF_3CF_2CF_2CH_2O-N=CH$)— | — | m.p. 60-62° C. |
| b-40 | — | O | *-C(Me)=CH-** | 4-($CF_3CF_2CH_2O-N=CH$) | — | m.p. 62-64° C. |
| b-41 | — | O | *-C(Me)=CH-** | 4-($CF_3CH_2O-N=CH$) | — | m.p. 125-127° C. |
| b-42 | — | O | *-C(Me)=CH-** | 4-(O=CH) | — | — |
| b-43 | 4-Me | O | *-C(Cl)=CH-** | 4-$CHF_2CF_2CH_2O$ | — | m.p. 136-138° C. |
| b-44 | — | O | *-C(Cl)=CH-** | 4-$CHF_2CF_2CH_2O$ | — | m.p. 133-135° C. |
| b-45 | 4-Me | O | *-C(Cl)=CH-** | 4-$CF_3CF_2CH_2O$ | — | m.p. 149-151° C. |
| b-46 | — | O | *-C(Cl)=CH-** | 4-$CF_3CF_2CH_2O$ | — | nD(20.3)1.4769 |
| b-47 | 4-Me | O | *-C(Cl)=CH-** | 4-$CF_3CH_2O$ | — | m.p. 181-183° C. |
| b-48 | — | O | *-C(Cl)=CH-** | 4-$CF_3CH_2O$ | — | m.p. 151-153° C. |

TABLE 1-continued

| Compound Number | $(X^1)_m$ | A | Y | $X^2$ | $(X^3)_n$ | Physical Properties |
|---|---|---|---|---|---|---|
| b-49 | — | O | *C(Me)=C**H (Me down) | 4-CF$_3$ | 2-Cl | m.p. 108-110° C. |
| b-50 | — | O | *C(Me)=C**H | 4-CF$_3$ | 3-Cl | m.p. 69-71° C. |
| b-51 | — | O | *C(Me)=C**H | 4-CF$_3$ | 2-F | m.p. 164-166° C. |
| b-52 | — | O | *C(Me)=C**H | 4-CF$_3$ | 3-F | m.p. 100-102° C. |
| b-53 | — | O | *C(Cl)=C**H | 4-CF$_3$ | 2-F | m.p. 121-123° C. |
| b-54 | — | O | *C(Cl)=C**H | 4-CF$_3$ | 2-Cl | m.p. 114-116° C. |
| b-55 | — | O | *C(Cl)=C**H | 4-CF$_3$ | 3-Cl | m.p. 117-119° C. |
| b-56 | — | O | *C(Cl)=C**H | 4-CF$_3$ | 3-F | m.p. 148-150° C. |

Example 2

Pyridin-1-ium-1-yl (6-(trifluoromethoxy)benzo[d]thiazole-2-carbonyl) amide

Synthesis of [pyridin-1-ium-1-yl (6-(trifluoromethoxy)benzo[d]thiazole-2-carbonyl) amide]

[Chemical Formula 25]

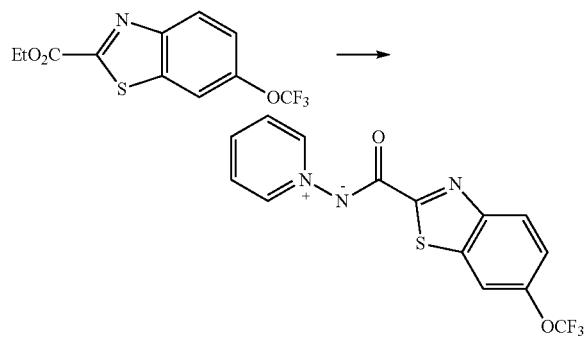

Ethyl 6-(trifluoromethoxy)benzo[d]thiazole-2-carboxylate (0.18 g) was dissolved in methanol (5 mL), a 2N aqueous solution of sodium hydroxide (2 mL) was added thereto at 0° C., and the resulting mixture was stirred for 30 minutes. Dilute hydrochloric acid was added thereto, and the resulting mixture was extracted with ethyl acetate. The organic layer was concentrated under reduced pressure. The concentrate was dissolved in dichloromethane (5 mL), oxalyl chloride (0.10 g) and DMF (one drop) were added thereto, and the resulting mixture was stirred for 1 hour. The solvent was distilled off therefrom under reduced pressure, the residue was dissolved in chloroform (5 mL), and 1-aminopyridinium iodide (0.14 g) and triethylamine (0.19 g) were added thereto. Water was added thereto, and the resulting mixture was extracted with dichloromethane. The organic layer was concentrated under reduced pressure. The desired product (0.09 g) was obtained by washing the concentrate with diethyl ether.

Examples of the compounds of the present invention produced by the same method as in the above Examples are shown in Table 2. Table 2 shows the compounds represented by the formula (I-2) among the compounds of the present invention. A bond marked with a symbol * in the formula (C) used for the notation of a partial structure of the compound is bonded to a carbonyl group or a thiocarbonyl group in a pyridinium salt.

(Chemical Formula 26)

(C)

Physical property data of the compounds were entered in the column of "Physical properties". As the physical property data, refractive indices (nD) or melting points (m.p.) were described.

NMR data for the compounds with compound numbers d-29, d-30, d-31, d-37, and d-38 are shown below.

d-29: $^1$H-NMR (CDCl$_3$, δ ppm) 5.01 (t, 2H), 7.72 (m, 2H), 7.95 (t, 1H), 8.43 (d, 1H), 8.77 (d, 1H), 8.81 (d, 2H).

d-30: $^1$H-NMR (CDCl$_3$, δ ppm) 5.03 (t, 2H), 7.71 (m, 2H), 7.92 (t, 1H), 8.46 (d, 1H), 8.78 (d, 1H), 8.85 (d, 2H).

d-31: $^1$H-NMR (CDCl$_3$, δ ppm) 5.01 (t, 2H), 7.70 (m, 2H), 7.85 (t, 1H), 8.32 (d, 1H), 8.76 (d, 1H), 8.79 (d, 2H).

d-37: $^1$H-NMR (CDCl$_3$, δ ppm) 1.34 (d, 6H), 3.10 (m, 1H), 4.95 (t, 2H), 7.53 (d, 2H), 8.42 (d, 1H), 8.61 (d, 2H), 8.77 (d, 1H).

d-38: $^1$H-NMR (CDCl$_3$, δ ppm) 4.14 (s, 3H), 4.99 (t, 2H), 7.20-7.28 (m, 2H), 8.02 (t, 1H), 8.28 (d, 1H), 8.44 (s, 1H), 8.78 (s, 1H).

[Chemical Formula 27]

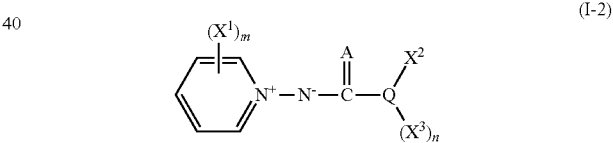
(I-2)

TABLE 2

| Compound Number | $(X^1)_m$ | A | (X³)ₙ) | Physical Properties |
|---|---|---|---|---|
| d-1 | — | O | *—(benzo[d]thiazol-2-yl with 6-OCF$_3$) | m.p 178-182° C. |
| d-2 | — | O | *—(benzo[d]thiazol-2-yl with 6-CF$_3$) | m.p 267-270° C. |

TABLE 2-continued
| Compound Number | (X¹)m | A | *—O—X² / (X³)n | Physical Properties |
|---|---|---|---|---|
| d-3 | — | O | 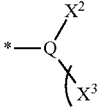 | m.p 210-213° C. |
| d-4 | — | O | 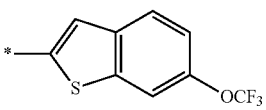 | m.p 205-207° C. |
| d-7 | — | O | 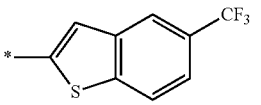 [SMILES: *c1cc2cc(C(F)(F)F)ccc2s1] | m.p 177-178° C. |
| d-8 | — | O | 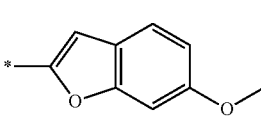 | m.p 264-266° C. |
| d-10 | — | O | 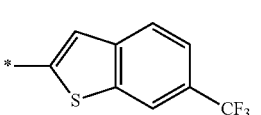 | m.p 190-192° C. |
| d-11 | — | O | 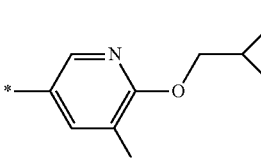 | m.p 188-190° C. |
| d-12 | — | O | 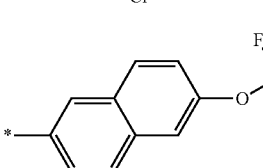 | m.p 177-179° C. |
| d-14 | — | O | 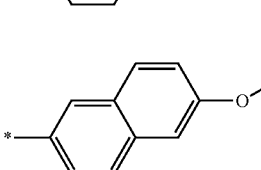 | m.p 154-156° C. |
| d-15 | — | O | 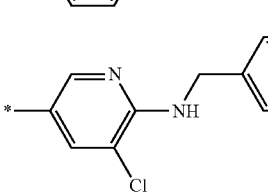 | m.p 150-152° C. |
| d-16 | — | O | 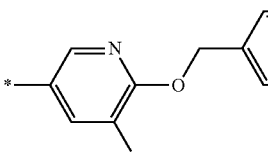 | m.p 80-82° C. |

TABLE 2-continued
| Compound Number | (X¹)m | A | [structure] | Physical Properties |
|---|---|---|---|---|
| d-17 | — | O | 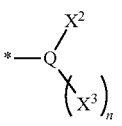 | nD(20.9)1.6022 |
| d-18 | 4-Me | O | 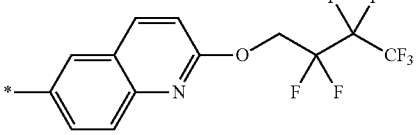 | m.p 155-157° C. |
| d-19 | 3-Me | O | 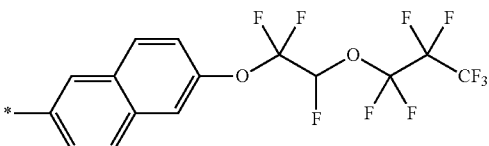 | m.p 134-136° C. |
| d-20 | 2-Me | O | 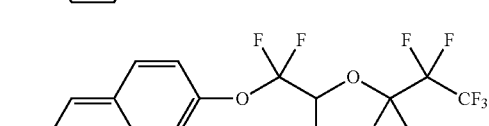 | m.p 53-55° C. |
| d-21 | — | O | 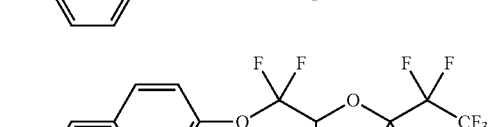 | m.p 177-179° C. |
| d-22 | — | O | 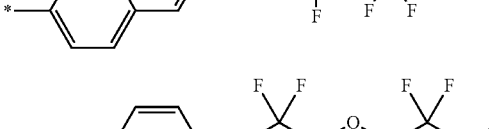 | m.p 140-142° C. |
| d-23 | — | O | 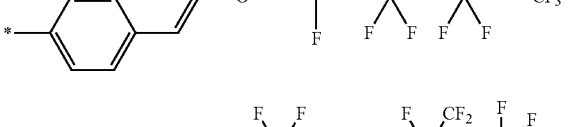 | m.p 136-138° C. |
| d-24 | — | O | 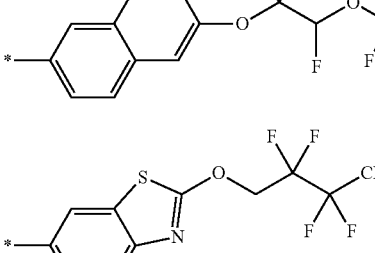 | m.p 122-124° C. |
| d-25 | 3-Me | O | 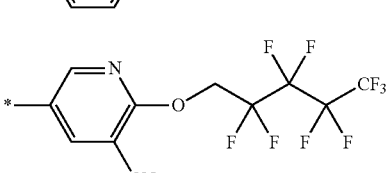 | nD(20.8)1.5928 |

TABLE 2-continued
| Compound Number | (X¹)m | A | structure | Physical Properties |
|---|---|---|---|---|
| d-26 | 2-Me | O | 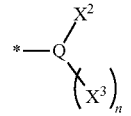 | nD(20.5)1.5844 |
| d-27 | 4-MeO | O | 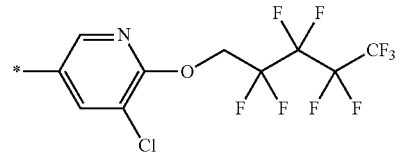 [SMILES: *c1cnc(OCC(F)(F)C(F)(F)C(F)(F)C(F)(F)F)c(Cl)c1] | m.p 171-173° C. |
| d-28 | — | O | 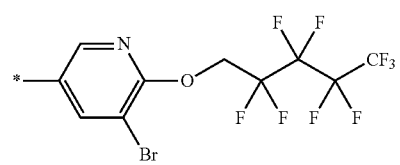 [SMILES: *c1cnc(OCC(F)(F)C(F)(F)C(F)(F)C(F)(F)F)c(Br)c1] | m.p 45-47° C. |
| d-29 | — | O | 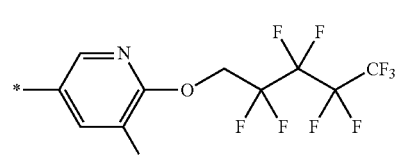 | — |
| d-30 | — | O | 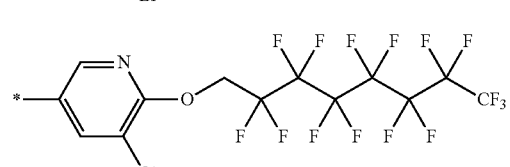 | — |
| d-31 | — | O | 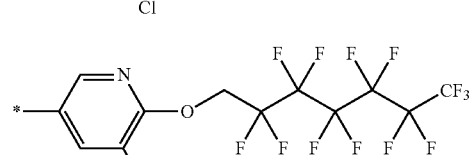 | — |
| d-32 | — | O | 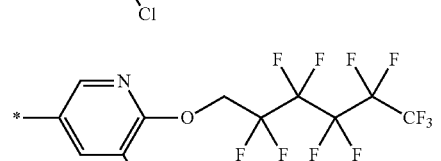 | m.p 78-80° C. |
| d-33 | — | O | 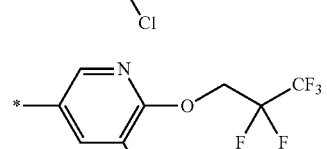 | m.p 154-156° C. |
| d-34 | — | O | 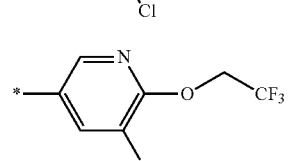 | m.p 123-124° C. |

TABLE 2-continued
| Compound Number | (X¹)m | A | (structure) | Physical Properties |
|---|---|---|---|---|
| d-35 | 4-MeO | O | 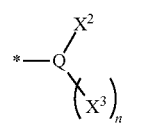 | m.p 110-113° C. |
| d-36 | — | O | 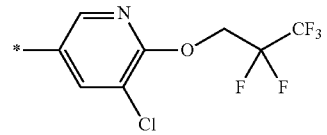 [SMILES: *c1cnc(OCC(F)(F)C(F)(F)F)c(Cl)c1] | m.p 117-119° C. |
| d-37 | 4-$^i$Pr | O | 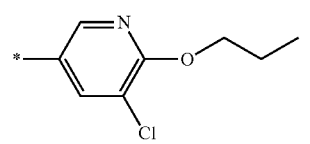 [SMILES: *c1cnc(OCCC)c(Cl)c1] | — |
| d-38 | 2-MeO | O | 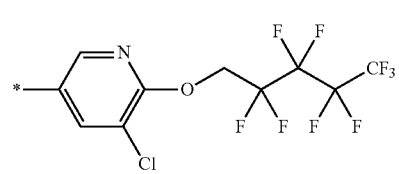 [SMILES: *c1cnc(OCC(F)(F)C(F)(F)C(F)(F)C(F)(F)F)c(Cl)c1] | — |
| d-39 | 4-Me | O | 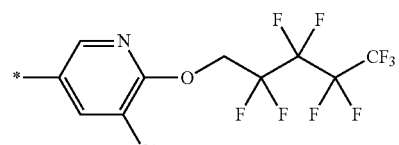 | m.p 97-99° C. |
| d-40 | 3-Cl | O | 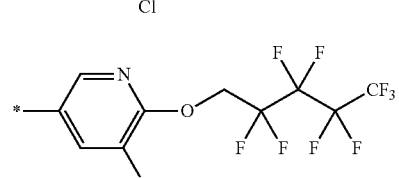 | m.p 102-103° C. |
| d-41 | 4-CF$_3$ | O | 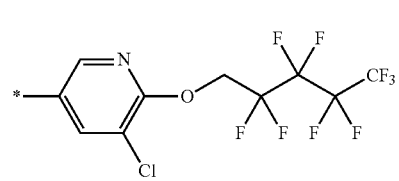 [SMILES: *c1cnc(OCC(F)(F)C(F)(F)C(F)(F)C(F)(F)F)c(Cl)c1] | m.p 124-125° C. |
| d-42 | 3-CF$_3$ | O | 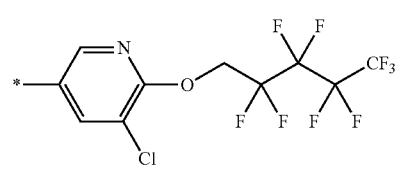 [SMILES: *c1cnc(OCC(F)(F)C(F)(F)C(F)(F)C(F)(F)F)c(Cl)c1] | m.p 155-156° C. |
| d-43 | 4-MeO | O | 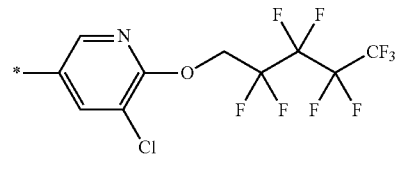 [SMILES: *c1cnc(OCC(F)(F)C(F)(F)C(F)(F)C(F)(F)F)c(Cl)c1] | m.p 119-121° C. |

TABLE 2-continued

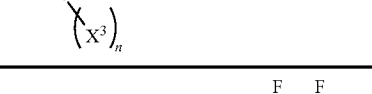

| Compound Number | (X¹)m | A | | Physical Properties |
|---|---|---|---|---|
| d-44 | 3-MeO | O | | m.p 109-110° C. |

Furthermore, a compound having the following structure (Compound No. d-45) is also shown. d-45 had a melting point of 165-167° C.

(Chemical Formula 28)

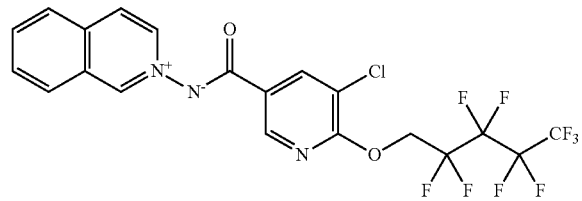

[Biological Test]

The following test examples show that the compounds of the present invention are useful as active ingredients of pest control agents. "Parts" are on a weight basis.

(Preparation of Test Emulsion)

5 parts by weight of the compound of the present invention, 93.6 parts by weight of dimethylformamide, and 1.4 parts by weight of polyoxyethylene alkylaryl ether were mixed and dissolved to prepare an emulsion (I) containing 5% of an active ingredient.

(1) Efficacy Test Against *Mythinma separata* Using Artificial Diet 0.8 g of a commercially available artificial diet (Insecta LFS, manufactured by Nosan Corporation) and 1 μl of the emulsion (I) were thoroughly mixed and 0.2 g per each treatment group was packed in a plastic test container (1.4 ml volume) to prepare a test diet.

Two second instar larvae of *Mythimna separata* were inoculated for each treatment group and sealed with a plastic lid. It was placed in a thermostatic chamber at 25° C., and the insecticidal rate and food intake were examined on the fifth day. The test was repeated twice. In addition, a test carried out under the same conditions except that the compound of the present invention was removed from the emulsion (I) was designated as a solvent control group.

TABLE 3

| Compound Number | | |
|---|---|---|
| b-5 | b-55 | d-31 |
| b-7 | b-56 | d-35 |
| b-9 | d-4 | d-37 |
| b-11 | d-8 | d-38 |
| b-13 | d-11 | d-39 |
| b-17 | d-12 | d-40 |
| b-18 | d-15 | d-41 |

TABLE 3-continued

| Compound Number | | |
|---|---|---|
| b-20 | d-15 | d-42 |
| b-21 | d-18 | d-43 |
| b-23 | d-19 | d-44 |
| b-28 | d-20 | d-45 |
| b-30 | d-21 | |
| b-38 | d-22 | |
| b-39 | d-24 | |
| b-40 | d-25 | |
| b-41 | d-26 | |
| b-44 | d-27 | |
| b-46 | d-28 | |
| b-50 | d-29 | |
| b-51 | d-30 | |

The compounds shown in Table 3 were tested for efficacy against *Mythinma separata*. All of the compounds were effective against *Mythimna separata*, with an insecticidal rate of 100% or a food intake of 10% or less, relative to the solvent control group.

(2) Efficacy Test Against *Mythimna Separata*

The emulsion (I) was diluted with water so that the concentration of the compound of the present invention was 125 ppm. Maize leaf pieces were immersed in the diluent for 30 seconds. The maize leaf pieces were placed in a petri dish, and five second instar larvae of *Mythimna separata* were released. The petri dish was placed in a thermostatic chamber at a temperature of 25° C. and a humidity of 60%. Viability was evaluated when 6 days had passed since the release of the insects, and the insecticidal rate was calculated. The test was repeated twice.

TABLE 4

| Compound Number |
|---|
| b-5 |
| b-9 |
| b-20 |
| b-21 |
| b-30 |
| d-2 |
| d-3 |
| d-4 |
| d-8 |
| d-16 |

The compounds shown in Table 4 were tested for efficacy against *Mythimna separata*. All compounds showed an insecticidal rate of 80% or more against *Mythimna separata*.

(3) Efficacy Test Against *Spodoptera litura*

The emulsion (I) was diluted with water so that the concentration of the compound of the present invention was 125 ppm. Cabbage leaves were immersed in the diluent for 30 seconds. The cabbage leaves were air dried and placed in a petri dish, and five second instar larvae of *Spodoptera litura* were released. The petri dish was placed in a thermostatic chamber at a temperature of 25° C. and a humidity of 60%. Viability was evaluated when 6 days had passed since the release of the insects, and the insecticidal rate was calculated. The test was repeated twice.

TABLE 5

| Compound Number | | |
|---|---|---|
| b-9 | d-8 | d-41 |
| b-11 | d-11 | d-42 |
| b-21 | d-15 | d-43 |
| b-23 | d-18 | d-45 |
| b-30 | d-19 | |
| b-31 | d-20 | |
| b-32 | d-21 | |
| b-37 | d-22 | |
| b-38 | d-23 | |
| b-39 | d-26 | |
| b-41 | d-27 | |
| d-1 | d-29 | |
| d-2 | d-30 | |
| d-3 | d-31 | |
| d-4 | d-38 | |

The compounds shown in Table 5 were tested for efficacy against *Spodoptera litura*. All compounds showed an insecticidal rate of 80% or more against *Spodoptera litura*.

(4) Efficacy Test Against *Plutella xylostella*

The emulsion (I) was diluted with water so that the concentration of the compound of the present invention was 125 ppm. Cabbage leaves were immersed in the diluent for 30 seconds. The cabbage leaves were air dried and placed in a petri dish, and five second instar larvae of *Plutella xylostella* were released. The petri dish was placed in a thermostatic chamber at a temperature of 25° C. and a humidity of 60%. Viability was evaluated when 3 days had passed since the release of the insects, and the insecticidal rate was calculated. The test was repeated twice.

TABLE 6

| Compound Number | |
|---|---|
| b-5 | d-38 |
| b-7 | d-39 |
| b-21 | d-40 |
| b-44 | d-41 |
| b-50 | d-42 |
| d-4 | d-43 |
| d-8 | d-44 |
| d-16 | |
| d-34 | |
| d-37 | |

The compounds shown in Table 6 were tested for efficacy against *Plutella xylostella*. All compounds showed an insecticidal rate of 80% or more against *Plutella xylostella*.

(5) Efficacy Test Against *Tetranychus urticae*

Kidney bean plants were raised in No. 3 pots, and five adult females of *Tetranychus urticae* were inoculated on primary leaves. The emulsion (I) was diluted with water so that the concentration of the compound of the present invention was 125 ppm. The diluent was sprayed on the kidney bean plants to prepare a treated group. In addition, a test was carried out under the same conditions except that the compound of the present invention was removed from the emulsion (I) to prepare a solvent control group. The above No. 3 pots were placed in a thermostatic chamber at a temperature of 25° C. and a humidity of 65%, and the inoculated adult females of *Tetranychus urticae* were removed 3 days after spraying, leaving only the eggs laid on the leaves. The number of individuals surviving on the leaves was investigated 10 days after spraying, and the control rate was calculated according to the following formula. The test was repeated twice.

$$\text{Control rate } (\%) = 100 \times [1 - Nt/Nc]$$

Nt: number of surviving individuals in treated group, Nc: number of surviving individuals in solvent control group

TABLE 7

| Compound Number |
|---|
| b-9 |
| b-11 |
| b-12 |
| b-13 |
| b-17 |
| b-18 |
| b-19 |
| b-20 |
| b-21 |
| b-31 |

The compounds shown in Table 7 were tested for efficacy against *Tetranychus urticae*. All compounds showed a control rate of 90% or more.

(6) Efficacy Test Against *Aphis gossypii*

Cucumber was sown in No. 3 pots. Adult females of *Aphis gossypii* were released on the cucumber 10 days after germination. The next day, the adult females were removed, leaving the first instar larvae produced. The emulsion (I) was diluted with water so that the concentration of the compound of the present invention was 125 ppm. This diluent was sprayed on the cucumber. Thereafter, the cucumber was placed in a thermostatic chamber at a temperature of 25° C. and a humidity of 60%, and after 5 days, the life and death of *Aphis gossypii* were investigated and the insecticidal rate was determined.

The compounds with compound numbers b-14, b-40, b-41, d-11, d-12, d-25, and d-38 were tested for efficacy against *Aphis gossypii*. All compounds showed an insecticidal rate of 80% or more.

(7) Efficacy Test Against *Helicoverpa armigera*

The emulsion (I) was diluted with water so that the concentration of the compound of the present invention was 125 ppm. Cabbage leaves were immersed in the diluent for 30 seconds. The cabbage leaves were air dried and placed in a petri dish, and five second instar larvae of *Helicoverpa armigera* were released. The petri dish was placed in a thermostatic chamber at a temperature of 25° C. and a humidity of 60%. Viability was evaluated when 6 days had passed since the release of the insects, and the insecticidal rate was calculated. The test was repeated twice.

The compounds with compound numbers b-39, b-40, and d-11 were tested for efficacy against *Helicoverpa armigera*. All compounds showed an insecticidal rate of 80% or more.

(9) Efficacy Test Against *Nilaparvata lugens*

The emulsion (I) was diluted with water so that the concentration of the compound of the present invention was 125 ppm. Rice seedlings were immersed in the diluent for 30 seconds, air dried, and then placed in a plastic case, and five second instar larvae of *Nilaparvata lugens* were released therein. The plastic case was stored in a thermostatic chamber at a temperature of 25° C. and a humidity of 65%, viability was evaluated 10 days after the inoculation, and the insecticidal rate was calculated by the following formula. The test was repeated twice.

Insecticidal rate (%)=(number of dead insects/number of tested insects)×100

The compounds with compound numbers b-50, b-55, and b-56 were tested for efficacy against *Nilaparvata lugens*. All compounds showed an insecticidal rate of 80% or more.

(10) Efficacy Test Against *Tetranychus kanzawai*

Mung bean plants were raised in No. 3 pots, and five adult females of *Tetranychus kanzawai* were inoculated on primary leaves. The emulsion (I) was diluted with water so that the concentration of the compound of the present invention was 125 ppm. The diluent was sprayed on the mung bean plants to prepare a treated group. In addition, a test was carried out under the same conditions except that the compound of the present invention was removed from the emulsion (I) to prepare a solvent control group. The above No. 3 pots were placed in a thermostatic chamber at a temperature of 25° C. and a humidity of 65%, and the inoculated adult females of *Tetranychus kanzawai* were removed 4 days after spraying, leaving only the eggs laid on the leaves. The number of individuals surviving on the leaves was investigated 11 days after spraying, and the control rate was calculated according to the following formula. The test was repeated twice.

Control rate (%) = 100 × [1 − Nt/Nc]

Nt: number of surviving individuals in treated group, Nc: number of surviving individuals in solvent control group

TABLE 8

| Compound Number | | |
|---|---|---|
| b-38 | b-51 | d-20 |
| b-39 | b-52 | d-21 |
| b-40 | b-53 | d-22 |
| b-41 | b-55 | d-26 |
| b-43 | b-56 | d-28 |
| b-44 | d-11 | d-39 |
| b-45 | d-12 | d-44 |
| b-46 | d-16 | |
| b-49 | d-18 | |
| b-50 | d-19 | |

The compounds shown in Table 8 were tested for efficacy against *Tetranychus kanzawai*. All compounds showed a control rate of 90% or more.

Since those randomly selected from among the pyridinium salts of the present invention exert the above-mentioned effects, it can be understood that the pyridinium salts of the present invention including the compounds that are not shown in examples are compounds having the effects of pest control, acaricidal effects, and in particular, insecticidal effects and the like.

INDUSTRIAL APPLICABILITY

It is possible to provide a pyridinium salt which is excellent in pest control activity, in particular, insecticidal activity and/or acaricidal activity, excellent in safety and can be synthesized in an industrially favorable manner. In addition, it is possible to provide a pest control agent, an insecticidal or acaricidal agent, an ectoparasite control agent, or an endoparasite control- or exterminating agent containing a pyridinium salt as an active ingredient.

The invention claimed is:

1. A compound represented by a formula (I-2) or a formula (II-2):

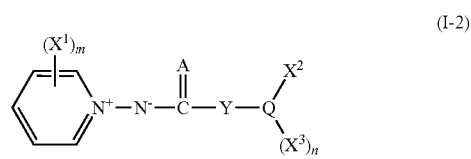

(I-2)

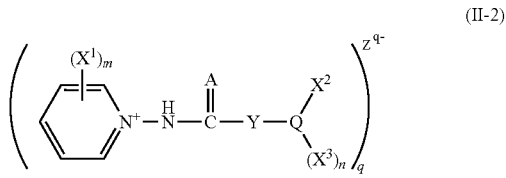

(II-2)

wherein

A represents an oxygen atom or a sulfur atom;

$X^1$ represents a halogeno group, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{1-6}$ alkoxy group, a substituted or unsubstituted $C_{2-6}$ alkenyloxy group, a substituted or unsubstituted $C_{2-6}$ alkynyloxy group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{3-8}$ cycloalkyl group, a substituted or unsubstituted $C_{6-10}$ aryl group, a substituted or unsubstituted $C_{6-10}$ aryloxy group, a substituted or unsubstituted 5- to 6-membered heteroaryl group, a substituted or unsubstituted 5- to 6-membered heteroaryloxy group, a group represented by $R^aR^bN$-, a group represented by $R^aR^bN$-CO-, a group represented by $R^cCO$-NH-, a pentafluorosulfanyl group, a nitro group or a cyano group;

$R^a$ represents a hydrogen atom, a substituted or unsubstituted $C_{1-6}$ alkyl group, or a substituted or unsubstituted $C_{6-10}$ aryl group, $R^b$ represents a hydrogen atom, a substituted or unsubstituted $C_{1-6}$ alkyl group, or a substituted or unsubstituted $C_{6-10}$ aryl group, $R^c$ represents a hydrogen atom, a substituted or unsubstituted $C_{1-6}$ alkyl group, or a substituted or unsubstituted $C_{6-10}$ aryl group, m represents the number of $X^1$ groups and is any integer of 0 to 5, Q represents a pyridine ring, $X^2$ represents a substituted or unsubstituted $C_{2-6}$ alkenyloxy group, a substituted or unsubstituted $C_{2-6}$ alkynyloxy group, a substituted or unsubstituted $C_{6-10}$ aryloxy group, or a substituted or unsubstituted 5- to 6-membered heteroaryloxy group $X^3$ represents a halogeno group, a substituted or unsubstituted $C_{1-6}$ alkyl group, a hydroxyl group, a substituted or unsubstituted $C_{1-6}$ alkoxy group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a pentafluorosulfanyl group, a nitro group, or a cyano group, n represents the number of $X^3$ groups and is any integer of 0 to 4, $Z^{q-}$ represents a counter ion, and q represents a valence of the counter ion and is 1 or 2.

2. A pest control agent comprising at least one selected from the compounds according to claim 1 as an active ingredient.

3. An insecticidal or acaricidal agent comprising at least one selected from the compounds according to claim 1 as an active ingredient.

4. An ectoparasite control agent comprising at least one selected from the compounds according to claim 1 as an active ingredient.

5. An endoparasite control or exterminating agent comprising at least one selected from the compounds according to claim 1 as an active ingredient.

\* \* \* \* \*